US008563588B2

(12) United States Patent
Carreaux et al.

(10) Patent No.: US 8,563,588 B2

(45) Date of Patent: Oct. 22, 2013

(54) IMIDAZOLONE DERIVATIVES, METHOD FOR THE PREPARATION THEREOF AND BIOLOGICAL APPLICATIONS

(75) Inventors: Francois Carreaux, Chateaugiron (FR); Jean-Pierre Bazureau, La Chappelle des Fougeretz (FR); Steven Renault, Pont l'Abbe (FR); Laurent Meijer, Roscoff (FR); Olivier Lozach, Plabennec (FR)

(73) Assignees: Universite de Rennes 1, Rennes Cedex (FR); Centre National de la Recherche Scientifique (C.N.R.S.), Paris Cedex (FR)

( * ) Notice: Subject to any disclaimer, the term of this patent is extended or adjusted under 35 U.S.C. 154(b) by 175 days.

(21) Appl. No.: 12/452,940

(22) PCT Filed: Aug. 1, 2008

(86) PCT No.: PCT/FR2008/001152

§ 371 (c)(1), (2), (4) Date: Apr. 26, 2010

(87) PCT Pub. No.: WO2009/050352

PCT Pub. Date: Apr. 23, 2009

(65) Prior Publication Data

US 2010/0216855 A1 Aug. 26, 2010

(30) Foreign Application Priority Data

Aug. 1, 2007 (FR) .................................... 07 05632

(51) Int. Cl.
*A61K 31/4166* (2006.01)
*C07D 233/70* (2006.01)

(52) U.S. Cl.
USPC .................................... 514/386; 548/316.4

(58) Field of Classification Search
USPC .................................... 548/316.4; 514/386
See application file for complete search history.

(56) References Cited

FOREIGN PATENT DOCUMENTS

| | | |
|---|---|---|
| EP | 0 102 026 | 3/1984 |
| EP | 0 422 900 | 4/1991 |
| EP | 0 728 747 | 8/1996 |
| EP | 1 484 051 | 12/2004 |
| JP | 2007-063444 | 3/2007 |
| WO | 2006/040052 | 4/2006 |
| WO | 2006/106046 A1 * | 10/2006 |
| WO | 2006/106046 | 12/2006 |
| WO | 2007/054508 | 5/2007 |
| WO | 2007/065261 | 6/2007 |

OTHER PUBLICATIONS

International Search Report for PCT/FR2008/001152, mailed Jun. 4, 2009.

Chemical Abstracts Service, Columbus, Ohio, US; Rajpuroht, Sangeeta et al., "Synthesis and Antimicrobial Activity of 5'-Aryl-Substituted (4"-Benzylidene-4, 5-dihydro-5-oxo-1-(H)-Imidazolo)-1",3",4"-Oxadiazoles" Accession No. 2006:61023 (2005).

Chemical Abstract Service, Columbus, Ohio, US; Solankee, Anjani et al., "Synthesis and Antimicrobial Activity of 1-phenyl/substituted phenyl/benzyl/naphthyl-2-Phenyl-4-(3-Phenoxybenzylidene) Imidazolin-5-Ones" Accession No. 2002:410854 (2002).

Chemical Abstracts Service, Columbus, Ohio, US; Al-Madi et al., "The in Vitro Antitumor Assay of 5-(Z)-Arylidene-4-Imidazolidiones in Screens of AIDS-Related Leukemia and Lymphomas" Accession No. 2002:30459 (2001).

Chemical Abstracts Service, Columbus, Ohio, US; Carter, Percy et al., "Photochemically Enhanced Binding of Small Molecules to the Tumor Necrosis Factor Receptor-1 Inhibits the Binding of TNF-Alpha.[Erratum to Document cited in CA136:95580]" Accession No. 2002:9462 (2001).

Chemical Abstracts Service, Columbus, Ohio, US; Khodair, Ahmed, "Synthesis of 2-Thiohydantoins and their S-Glucosylated Derivatives as Potential Antiviral and Antitumor Agents" Accession No. 2001: 710919 (2001).

Chemical Abstracts Service, Columbus, Ohio, US; Cherouvier Jean Rene et al., "A Stereoselective Route to 3-Methyl-2-Methylsulfanyl-5-Ylidene-3, 5-Dihydroimidazol-4-one Derivatives and Precursor of Leucettamine B" Accession No. 2001:601202 (2001).

Chemical Abstracts Service, Columbus, Ohio; US; Solankee, Anjani et al., "Synthesis and Antimicrobial Activity of 1-(phenyl- and Substituted Phenyl)-2-Phenyl-4-(3',4',5'-Trisubstituted Benzylidene)-5-Imidazolanes" Accession No. 2000:391713 (2000).

Chemical Abstracts Service, Columbus, Ohio, US; Bharathi, K. et al., "Synthesis Pharmacological evaluation and QSAR Studies of 4,5-Dihydro-4-[(Substituted Phenyl) Methylene]-5-oxo-2-Phenyl/Methyl-1H-imidazole-1-Acetic Acids" Accession No. 1999:669507 (1999).

Chemical Abstracts Service, Columbus, Ohio, US; Soni et al., "Synthesis and Antimicrobial Activity of some new Imidazolones having Chloramphenicol Base Moiety" Accession No. 1992L 151653 (1991).

(Continued)

*Primary Examiner* — Kamal Saeed
*Assistant Examiner* — Janet L Coppins
(74) *Attorney, Agent, or Firm* — Nixon & Vanderhye P.C.

(57) ABSTRACT

Imidazolone derivatives, as medicaments, of formula

I

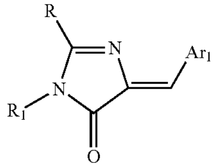

wherein:

$R_1$=H, $C_1$ to $C_5$ alkyl, aryl or a 5- or 6-membered heterocyclic group;

$Ar_1$=optionally substituted aryl or an aromatic heterocycle;

R=$R_2$—S—, $R_3$—HN—, $R_4$COHN or $Ar_2$, with $R_2$=a $C_1$-$C_5$ alkyl, vinyl or vinyl($C_1$-$C_5$)alkyl, nitrile or nitrile($C_1$-$C_5$)alkyl, aryl or benzyl radical, which are optionally substituted;

$R_3$=the meanings given above and H;

$Ar_2$=substituted or unsubstituted aryl.

4 Claims, 1 Drawing Sheet

(56) References Cited

OTHER PUBLICATIONS

Chemical Abstracts Service, Columbus, Ohio, US; Bousquet, E. et al., "Synthesis and Antiarrhythmic Activity of 5-Benzylidenimidazolin-4- One Derivatives" Accession No. 1979: 468308 (1979).

Chemical Abstracts Service, Columbus, Ohio, US; Kuchar et al., Synthesis and Antiinflammatory Effect of 1-(ethoxycarbonylmethyl) Imidazolin-5-one Derivatives. Accession No. 1976:446500 (1975).

Chemical Abstracts Service, Columbus, Ohio, US; Sah, Pramilla et al., "Antimicrobial Activity of Some Imidazolo Substituted 4-Thiazolidinones" Accession No. 2007:318949 (2006).

Chemical Abstracts Service, Columbus, Ohio, US; Saravanan, Sampath et al., "Synthesis and Antibacterial Activity of some Imidazole-5-(4H) one Derivatives" Accession No. 2005:1214648 (2005).

Chemical Abstracts Service, Columbus, Ohio, US; Gupta, J. K. et al., "Pharmacological Evaluation of Synthetic Imidazolinones and their Schiff Bases" Accession No. 2005:966275 (2005).

Chemical Abstracts Service, Columbus, Ohio, US; Kie-Kononowicz, Katarzyna et al., "Preparation of Novel 5-Arylidene-4-oxo-2-Imidazolidinylglycines as Anticonvulsants" Accession No. 2005: 904548 (2004).

Chemical Abstracts Service, Columbus, Ohio, US; Saravanan, V. S. et al., "Synthesis and Antiinflammatory Activity of some Analogues of 4-Substituted-2-Phenyl Imidazolin-5 (4H)-one Derivatives" 2005: 38341 (2005).

Chemical Abstracts Service, Columbus, Ohio, US; Hoharam , Hosny Hamed: "Process for the Synthesis of 5-(4-Dimethylaminobenzylidene)2-Phenylhydrazino[(1, 3-H]imidazole-4-one as Antitumor Agent". Accession No. 2003:991890 (2001).

Harolak-Wojciechowska, Janina et al., "Structure and Activity Studies of Glycine Receptor Ligands. Part 8. Arylidene-Imidazoline-4-one Amino Acids", Journal of Molecular Structure, vol. 649, No. 1-2, 2003, pp. 25-36.

Chemical Abstracts Service, Columbus, Ohio, US; Chazeau, V. et al., "Study of 5-Arylidene-2-Thiohydantoins with Potential Immunomodulating and Anticancer Activities" Accession No. 1993:124447 (1992).

Chemical Abstracts Service, Columbus, Ohio, US; Watanabe, Kinzo et al., "A new Bioactive Triene Aldehyde from the Marine Sponge Leucetta Microraphis" Accession No. 2000:3593 (2000).

Chemical Abstracts Service, Columbus, Ohio, US; Renault, Steven et al., "Parallel Solution-Phase Synthesis of 2-Alkylthio-5-Arylidene-3, 5-Dihydro-4H-Imidazol-4-one by One-Pot Three-Component Domino Reaction" Accession No. 2007:1003123 (2007).

Chemical Abstracts Service, Columbus, Ohio, US; Cherouvrier, Jean Rene et al., "A Practical and Stereoselective Route to 5-Ylidene-3, 5-Dihydroimidazol-4-one Derivatives using Solvent-free Conditions under Focused Microwave Irradiations" Accession No. 2005: 618472 (2004).

Chemical Abstracts Service, Columbus, Ohio, US; Cherouvrier, Jean Rene et al., "Microwave-mediated Solventless Synthesis of new Derivatives of Marine Alkaloid Leucettamine B" Accession No. 2002: 303968 (2002).

Chemical Abstracts Service, Columbus, Ohio, US; Roue, Nathalie et al., "Synthesis of the Marine Aklaloid Leucettamine B" Accession No. 1999:798095 (1999).

Chemical Abstracts Service, Columbus, Ohio, US; Shafi, P. M. et al., "A new Synthetic Route to 4-Arylidene-2-Phenyl-2-Imidazolin-5-ones" Accession No. 1999:467108 (1999).

Chemical Abstracts Service, Columbus, Ohio, US; Sobha, T. D. et al., "Synthesis of Acylamino Acid Amides and Acylamino Acids by he Simultaneous Reduction and Hydrolysis of Imidazolinones" Accession No. 1998: 658114 (1998).

* cited by examiner

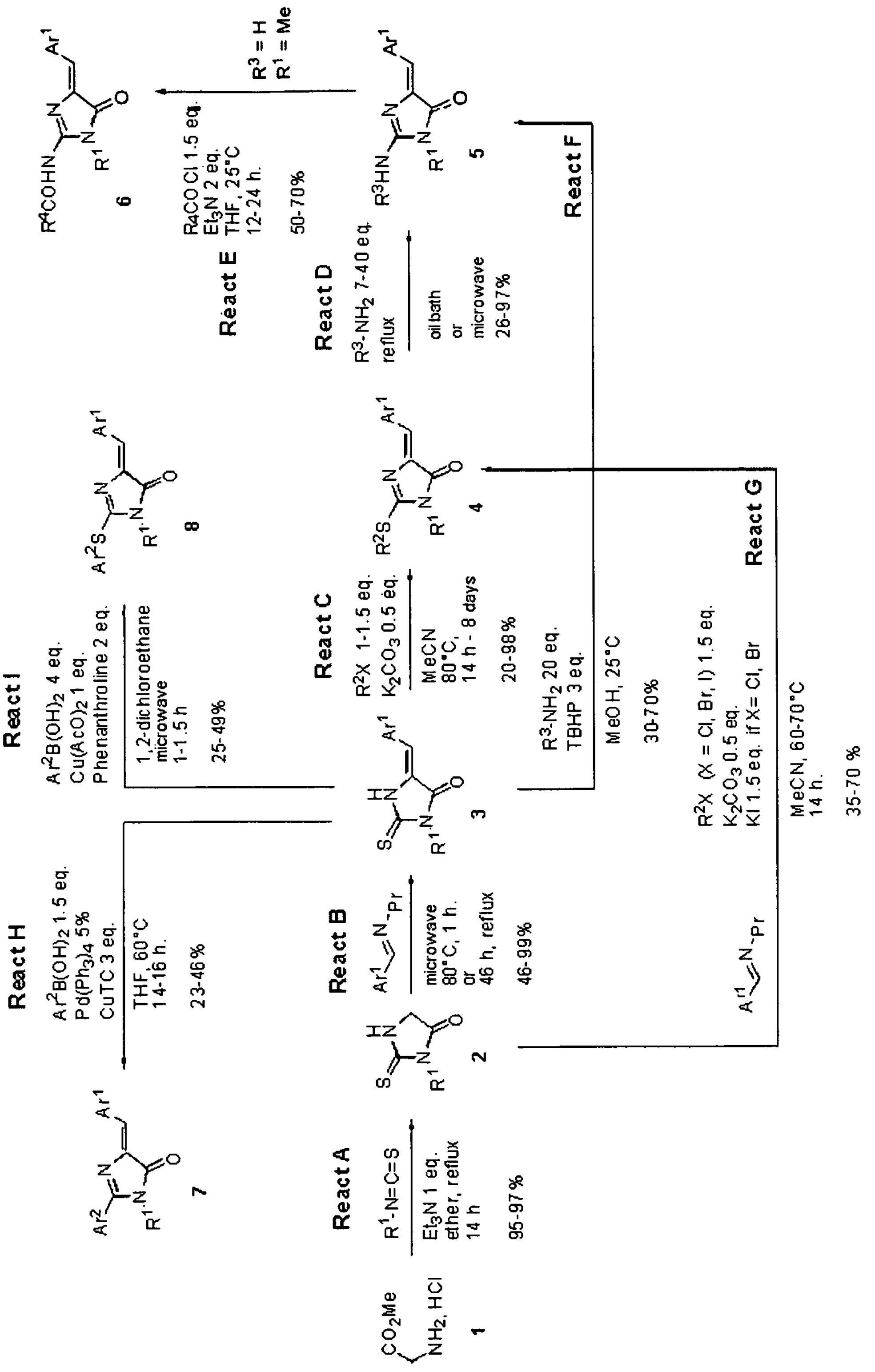
1
2
3
4
5
6
7
8
React A
$R^1$-N=C=S
$Et_3N$ 1 eq.
ether, reflux
14 h
95-97%
React B
microwave
80°C, 1 h.
or
46 h, reflux
46-99%
React C
$R^2X$ 1-1.5 eq.
$K_2CO_3$ 0.5 eq.
MeCN
80°C,
14 h - 8 days
20-98%
React D
$R^3$-$NH_2$ 7-40 eq.
reflux
oilbath
or
microwave
26-97%
React E
R4COCl 1.5 eq.
$Et_3N$ 2 eq.
THF, 25°C
12-24 h.
50-70%
$R^3$ = H
$R^1$ = Me
React F
$R^3$-$NH_2$ 20 eq.
TBHP 3 eq.
MeOH, 25°C
30-70%
React G
$R^2X$ (X = Cl, Br, I) 1.5 eq.
$K_2CO_3$ 0.5 eq.
KI 1.5 eq. if X= Cl, Br
MeCN, 60-70°C
14 h.
35-70 %
React H
$Ar^2B(OH)_2$ 1.5 eq.
$Pd(Ph_3)_4$ 5%
CuTC 3 eq.
THF, 60°C
14-16 h.
23-46%
React I
$Ar^2B(OH)_2$ 4 eq.
$Cu(AcO)_2$ 1 eq.
Phenanthroline 2 eq.
1,2-dichloroethane
microwave
1-1.5 h
25-49%

IMIDAZOLONE DERIVATIVES, METHOD FOR THE PREPARATION THEREOF AND BIOLOGICAL APPLICATIONS

This application is the U.S. national phase of International Application No. PCT/FR2008/001152, filed 1 Aug. 2008, which designated the U.S. and claims priority to French Application No. 0705632, filed 1 Aug. 2007, the entire contents of each of which are hereby incorporated by reference.

The subject of the invention is imidazolone derivatives. The invention also relates to a method for the preparation thereof.

It also relates to the biological uses of these derivatives as kinase inhibitors, in particular for the treatment of neurodegenerative diseases (especially Alzheimer's disease, Pick's disease and trisomy 21).

The vast majority of human pathological conditions involve phosphorylation abnormalities, often associated with abnormalities in regulation of certain protein kinases.

The search for effective inhibitors of these kinases has thus been very active over the past few years.

Using their long experience concerning kinases, CDKs, GSK-3 and CK1 as a basis for support, the inventors have focused on the production of inhibitors selective for the DYRK1A kinase (Dual-specificity Tyrosine-phosphorylation-Regulated Kinase 1 A).

It is an enzyme which autophosphorylates on its Tyrosine 321 (thereby resulting in its activation) and which phosphorylates Serine and Threonine residues.

The DYRK1A protein kinase gene is located in a quite specific region of chromosome 21, the "Down's syndrome critical region", which covers about 20 genes responsible for the trisomic phenotype. Many arguments support the hypothesis that even a modest (×1.5) overexpression of DYRK1A makes an essential contribution to the abnormal development of the brain observed during trisomy 21. Moreover, DYRK1A also appears to be highly involved in Alzheimer's disease (which appears in individuals suffering from trisomy 21 systematically and early after the age of about 40) (Kimura R, et al., 2006. The DYRK1A gene, encoded in chromosome 21 Down syndrome critical region, bridges between beta-amyloid production and tau phosphorylation in Alzheimer disease. Hum Mol Genet. 16, 15-23; Ferrer I, et al., 2005. Constitutive Dyrk1A is abnormally expressed in Alzheimer disease, Down syndrome, Pick disease, and related transgenic models. Neurobiol Dis. 20, 392-400).

DYRK1A inhibitors have been sought by virtual screening in silico on a structural model of DYRK1A based on the crystalline structure of GSK-3 (Kim et al., Bioorg. Med. Chem. Lett., 2006 Jul. 15; 16 (14):3712-6). In this approach, out of the 182 compounds selected, only 11 molecules showed an inhibitory activity with an $IC_{50}$ ranging from 2.5 to 50 μM.

The studies by the inventors in order to search for, optimize and characterize pharmacological inhibitors of the DYRK1A kinase have led them to discover that imidazolone derivatives corresponding to derivatives or analogs of leucettamine B constitute, in this respect, potent and selective pharmacological inhibitors of the DYRK1A kinase. Hereinafter, the term "compounds" will also be used to denote these derivatives and analogs as a whole.

Leucettamine B is a marine alkaloid extracted from the sponge *Leucetta microraphis*, of formula A (A)

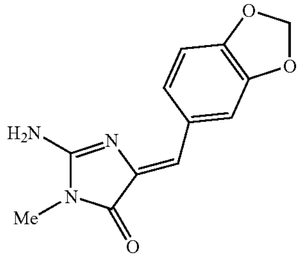

Leucettamine B

Research development has led the inventors to set up synthesis pathways for obtaining a family of compounds having inhibitory properties of great interest with respect to DYRK1A, with $IC_{50}$ values of mostly less than 50 μM and even than 10 μM, or even 1 μM.

The invention therefore relates to the use, as medicaments, of imidazolone derivatives constituting leucettamine B analogs and derivatives.

It also relates to a process for preparing these compounds.

The invention also relates to the compounds which correspond to novel imidazolone derivatives and to the uses thereof as active ingredients of medicaments.

According to a first aspect, the invention thus relates to the use, for producing medicaments for the treatment of neurodegenerative diseases, of imidazolone derivatives corresponding to formula (I)

(I)

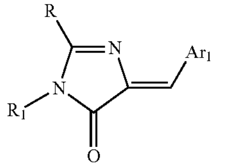

in which:

- $R_1$ represents H, a linear or branched, optionally substituted, $C_1$ to $C_5$ alkyl radical; an aryl group, or a 5- or 6-membered heterocyclic group, the aryl group and the heterocyclic group optionally comprising one or more substituents, which may be identical or different, occupying any positions;
- $Ar_1$ represents an aryl group with optionally one or more substituents, it being possible for two adjacent substituents to form a 5- or 6-membered ring, this ring being, where appropriate, substituted; or an aromatic heterocycle with optionally one or more substituents and/or condensed with a 5- or 6-membered aromatic ring, the heteroatom being chosen from N, S and O;
- R represents $R_2$—S—, $R_4COHN$ or $Ar_2$, with
  - $R_2$=a linear, branched or cyclic $C_1$-$C_5$ alkyl radical; a vinyl or vinyl($C_1$-$C_5$)alkyl radical, a nitrile or nitrile ($C_1$-$C_5$)alkyl radical, or an aryl or benzyl radical, said radicals being optionally substituted on one or more carbon atoms with one or more groups, which may be identical or different, occupying any positions, it being possible for two adjacent substituents to form a 5- or 6-membered ring, this ring being, where appropriate, substituted, $R_3$=the meanings given above and may also represent H;

$Ar_2$ representing a substituted or unsubstituted aryl radical, it being possible for two adjacent substituents to form a 5 or 6-membered ring, this ring being optionally substituted.

The invention also relates to the racemic forms of the above derivatives and also the enantiomeric forms thereof taken individually.

As illustrated by the examples, the above derivatives more especially constitute selective inhibitors of the DYRK1A kinase with $IC_{50}$ values of less than 5 μM, or even less than 1 μM, particularly advantageous derivatives having $IC_{50}$ values of less than 0.1 μM.

In formula (I) above, "aryl" represents phenyl or naphthyl and "heterocycle" represents a 5- or 6-membered ring with N, O and/or S as heteroatom(s). The substituents of $R_1$, $Ar_1$, $Ar_2$ and R are chosen from: OH, OZ, COH, COZ, COOH, COOZ, $NH_2$, NHalk., $N(alk.)_2$, NHCOOH, NHCOOZ, Z representing a linear or branched $C_1$-$C_5$ alkyl, aryl, benzyl, substituted benzyl or aryl, or benzodioxolyl radical, one or more halogens and/or a $CCl_3$ group, and alk. representing a $C_1$-$C_3$ alkyl radical.

The invention relates more especially, for use as medicaments, to imidazalone derivatives having an $IC_{50}$ of less than 5 μM and corresponding to formula I above in which:

$R_1$ represents a $C_1$-$C_3$ alkyl radical or a hydrogen atom, and/or an aryl radical, $Ar_1$ is chosen from

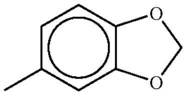,
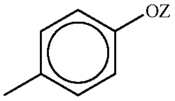 or
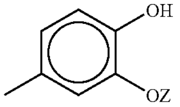

R represents an $R_2$—S— group, $R_2$ then being chosen from radicals of $T_1$-$(CH_2)_n$ type, with n=0, 1, 2 or 3 and $T_1$ representing one of the following radicals: methyl, vinyl, alkyl, alkynyl, nitrile, cycloalkyl, which may be $C_3$ or $C_4$, Z—O, Z—CO, with Z=$C_1$-$C_3$ alkyl, or hal, hal representing F, Cl, Br or I or a $CCl_3$ group, or an $R_3$—NH— group, $R_3$ then being chosen from radicals of $T_2$-$(CH_2)_n$ type, with n=0, 1 or 2, and $T_2$ representing one of the following radicals: methyl, vinyl, ZO, ZO—CONH—, —CH—$(OZ)_2$, ZCO, with Z=H or linear or branched $C_1$-$C_4$ alkyl, $NH_2$, $C_3$ cycloalkyl, aryl, or substituted aryl, or $R_2$=H, or an $R_4$—CONH— group, $R_4$ then being a branched $C_3$-$C_5$ alkyl radical, or R=$Ar_2$, $Ar_2$ being chosen from a phenyl, substituted phenyl or benzodioxolyl radical.

Preferably, the invention relates, for use as medicaments, to imidazolone derivatives having an $IC_{50}$ of less than 1 μM and corresponding to formula I in which:

$R_1$ represents H or $CH_3$ $Ar_1$ represents the radical

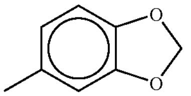 or 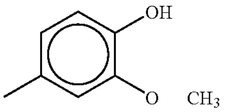

$R_2$ represents an $R_2$—S— group, $R_2$ then being chosen from radicals of $T_1$-$(CH_2)_n$ type, with $T_1$=a methyl, alkynyl, nitrile, hal, $CH_3O$, cyclopropyl or cyclobutyl radical, n=0, 1, 2 or 3, "hal" representing a halogen atom or a $CCl_3$ group, or an $R_3$—HN— group, $R_3$ then being chosen from radicals of $T_2$-$(CH_2)_n$ type, with $T_2$=$C_3$ alkyl, OH, cyclopropyl, phenyl, phenyl substituted with OH, $OCH_3$, COOH and OH, $CH_2OH$, $C(CH_3, OH)$, $CH_2$—$CH_2OH$, $CH_2$—COOH or benzodioxolyl, or $R_3$=H, n=0, 1 or 2, or an $Ar_2$ group chosen from a para-hydroxyphenyl or benzodioxolyl group.

In one preferred group of imidazolone derivatives of formula (I),

R represents $R^2S$, $R^3HN$, or $Ar^2$;

$R^1$ represents H or a linear or branched $C_1$-$C_5$ alkyl radical;

$R^2$ represents H or a linear or branched $C_1$-$C_5$ alkyl radical, where appropriate substituted with one or more OH, $C_1$-$C_5$ alkoxy, $(CH_2)_n$—OH or $(CH_2)_n$—COOH radicals; or represents a cyclic radical, where appropriate of the —$(CH_2)_n$— cycloalkyl type, the cycloalkyl radical having 3 to 5 members and n=1-5, the cyclic radical being, where appropriate, substituted with a $C_1$-$C_5$ alkyl; or represents a $(C_1$-$C_5)$alkylenenitrile; $(C_1$-$C_5)$alkylenevinyl; or $C_1$-$C_5$ alkynyl radical;

$R^3$ represents a linear or branched $C_1$-$C_5$ alkyl radical, where appropriate substituted with one or more $C_1$-$C_5$ alkoxy, OH, or COOH radicals; or represents a cyclic radical, where appropriate of the —$(CH_2)_n$— cycloalkyl type; or represents a phenyl radical, where appropriate substituted with one or more —OH, $(CH_2)_n$—OH; alkoxy or COOH; or a benzodioxolyl radical; or represents a cyclic radical, where appropriate of the —$(CH_2)_n$-cycloalkyl type, the cycloalkyl radical having 3 to 5 members, and n=1-5; or $NH_2$;

$Ar^1$ represents a benzodioxolyl radical;

$Ar^2$ represents a benzodioxolyl or phenyl radical, the latter being, where appropriate, substituted with one or more —OH or alkoxy.

In another preferred group of imidazolone derivatives of formula (I),

R represents $R^2S$, $R^3HN$, or $Ar^2$;

$R^1$ represents H or a linear or branched $C_1$-$C_5$ alkyl radical;

$R^2$ represents a linear or branched $C_1$-$C_5$ alkyl radical, where appropriate substituted with one or more OH, $C_1$-$C_5$ alkoxy or $(CH_2)_n$—OH radicals; or represents a cyclic radical, where appropriate of the —$(CH_2)_n$— cycloalkyl type, the cycloalkyl radical having 3 to 5 members, and n=1-5; or represents a $(C_1$-$C_5)$alkylenenitrile radical or a $(C_1$-$C_5)$alkylenevinyl radical;

$R^3$ represents a phenyl radical, where appropriate substituted with one or more —OH, $(CH_2)_n$—OH; alkoxy; or a benzodioxolyl radical; or represents a cyclic radical, where appropriate of the —$(CH_2)_n$-cycloalkyl type, the cycloalkyl radical having 3 to 5 members, and n=1-5; or $NH_2$;

$Ar^1$ represents a benzodioxolyl radical;

$Ar^2$ represents a benzodioxolyl or phenyl radical, the latter being, where appropriate, substituted with one or more —OH.

Particularly advantageously, the imidazolone derivatives used according to the invention are chosen from the following compounds in which, in formula (I),

R=$R_2$S $R_2$=$CH_2C{\equiv}CH$; $R_1$=Me; $Ar_1$=1,3-benzodioxol-5-yl $R_2$=$CH_2C{\equiv}N$; $R_1$=Me; $Ar_1$=1,3-benzodioxol-5-yl $R_2$=$CH_2CH_2Cl$; $R_1$=Me; $Ar_1$=1,3-benzodioxol-5-yl $R_2$=$CH_3$; $R_1$=H; $Ar_1$=1,3-benzodioxol-5-yl $R_2$=$CH_2CH_3$; $R_1$=H; $Ar_1$=1,3-benzodioxol-5-yl $R_2$=$CH_2CH_2CH_3$; $R_1$=H; $Ar_1$=1,3-benzodioxol-5-yl $R_2$=$CH(CH_3)_2$; $R_1$=H; $Ar_1$=1,3-benzodioxol-5-yl $R_2$=$CH_2C{\equiv}T$; $R_1$=H; $Ar_1$=1,3-benzodioxol-5-yl $R_2$=$CH_2(CH_2)_2$; $R_3$; $R_1$=H; $Ar_1$=1,3-benzodioxol-5-yl $R_2$=$CH_2CH_2OCH_3$; $R_1$=H; $Ar_1$=1,3-benzodioxol-5-yl $R_2$=$CH_2T_1$ with $T_1$=cyclopropyl; $R_1$=H; $Ar_1$=1,3-benzodioxol-5-yl $R_2$=$CH_2T_1$ with $T_1$=cyclobutyl; $R_1$=H; $Ar_1$=1,3-benzodioxol-5-yl

R=$R_3$NH $R_3$=$CH_2CH_3$; $R_1$=Me; $Ar_1$=1,3-benzodioxol-5-yl $R_3$=$CH_2CH_2OH$; $R_1$=Me; $Ar_1$=1,3-benzodioxol-5-yl $R_3$=$CH_2T_1$ with $T_1$=cyclopropyl; $R_1$=Me; $Ar_1$=1,3-benzodioxol-5-yl $R_3$=$CH_2CH_3$; $R_1$=Me; $Ar_1$=1,3-benzodioxol-5-yl $R_3$=o-HO—$C_6H_4$; $R_1$=Me; $Ar_1$=1,3-benzodioxol-5-yl $R_3$=$C_6H_5$; $R_1$=Me; $Ar_l$=1,3-benzodioxol-5-yl $R_3$=p-HO—$C_6H_4$; $R_1$=Me; $Ar_1$=1,3-benzodioxol-5-yl $R_3$=p-HO-m-$HO_2C$—$C_6H_3$; $R_1$=Me; $Ar_1$=1,3-benzodioxol-5-yl $R_3$=p-m-$OCH_2O$—$C_6H_3$; $R_1$=Me; $Ar_1$=1,3-benzodioxol-5-yl $R_3$=p-$CH_3$—$C_6H_4$; $R_1$=Me; $Ar_1$=1,3-benzodioxol-5-yl $R_3$=$HOCH_2CHOHCH_2$; $R_1$=Me; $Ar_1$=1,3-benzodioxol-5-yl $R_3$=p-m-$OCH_2CH_2O$—$C_6H_3$; $R_1$=Me; $Ar_1$=1,3-benzodioxol-5-yl $R_3$=p-$CH_3O$—$C_6H_4$; $R_1$=Me; $Ar_1$=1,3-benzodioxol-5-yl $R_3$=m-$HOCH_2$—$C_6H_4$; $R_1$=Me; $Ar_1$=1,3-benzodioxol-5-yl $R_3$=m-$HOCH(CH_3)$—$C_6H_4$; $R_1$=Me; $Ar_1$=1,3-benzodioxol-5-yl $R_3$=p-$HOCH_2CH_2$—$C_6H_4$; $R_1$=Me; $Ar_1$=1,3-benzodioxol-5-yl $R_3$=p-$HO_2CCH_2O$—$C_6H_4$; $R_1$=Me; $Ar_1$=1,3-benzodioxol-5-yl $R_3$=$CH_2CH_2CH_3$; $R_1$=H; $Ar_1$=1,3-benzodioxol-5-yl $R_3$=$CH_2T_1$ with $T_1$=cyclopropyl; $R_1$=H; $Ar_1$=1,3-benzodioxol-5-yl $R_3$=$C_6H_5$; $R_1$=H; $Ar_1$=1,3-benzodioxol-5-yl $R_3$=p-HO—$C_6H_4$; $R_1$=H; $Ar_1$=1,3-benzodioxol-5-yl $R_3$=H; $R_1$=H; $Ar_1$=p-HO-m-MeO—$C_6H_3$ R=$Ar_2$ $Ar_2$=p-HO—$C_6H_4$; $R_1$=Me; $Ar_1$=1,3-benzodioxol-5-yl $Ar_2$=p-m-$OCH_2O$—$C_6H_3$; $R_1$=Me; $Ar_1$=1,3-benzodioxol-5-yl According to another aspect, the invention relates to novel imidazolone derivatives.

In fact, with the exclusion of the derivatives mentioned hereinafter, the derivatives of formula I above are new derivatives and, in this respect, are part of the field of the invention.

The invention thus relates, as novel products, to imidazolone derivatives, characterized in that they correspond to formula I of claim 1, with the exclusion of the derivatives in which:

R=$R_2$S and $Ar_1$=1,3-benzodioxol-5-yl; $R_1$=$CH_3$ and $R_2$=$CH_3$, $CH_3CH_2$, $CH_2$=CH—$CH_2$, CH≡C—$CH_2$, $CH_3$—$CH_2$—OCO—$CH_2$, $C_6H_4$—$CH_2$ $Ar_1$=p, m-$OCH_3$; $R_1$=$CH_3$ and $R_2$=$CH_3CH_2$ $Ar_1$=m, m'-$OCH_3C_6H_4$; $R_1$=$CH_3$ and $R_2$=$CH_3CH_2$ $Ar_1$=1,3-benzodioxol-5-yl; $R_1$=n-butyl; $R_2$=$CH_3$, $CH_3$—$CH_2$, $CH_2$=CH—$CH_2$, CH≡$CH_2$, $C_6H_4$—$CH_2$, p $NO_2$—$C_6H_4$—$CH_2$, $CH_3CH_2OCO$—$CH_2$ $Ar_1$=1,3-bromobenzodioxol-5-yl; $R_1$=n butyl; $R_2$=$CH_3$—$CH_2$ $Ar_1$=m, p $OCH_3$—$C_6H_4$; $R_1$=n butyl; $R_2$=$CH_3CH_2$ $Ar_1$=1,3-benzodioxol-5-yl; $R_1$=$CH_3$; $R_2$=$C_6H_5$ or p-$OHC_6H_4$ R=$R_3$HN and $Ar_1$=1,3-benzodioxol-5-yl; $R_1$=$CH_3$; $R_2$=H, $CH_3$—$(CH_2)_2$, $CH_3$—$(CH_2)_3$, p COOH—$C_6H_4$—$CH_2$ $Ar_1$=1,3-benzodioxol-5-yl; $R_1$=$CH_3$—$(CH_2)_3$; $R_2$=$CH_3$—$(CH_2)_2$ or $CH_3$— $(CH_2)_3$ $Ar_1$=1,3-benzodioxol-5-yl; $R_1$=$C_6H_5$, $R_2$=$CH_3$—$(CH_2)_2$ $Ar_1$=p OH, m-$OCH_3$—$C_6H_4$ or m, p OH—$C_6H_4$; $R_1$=H; $R_2$=H.

These novel derivatives, in the use thereof as medicaments, are also part of the invention.

The invention therefore relates to pharmaceutical compositions comprising a therapeutically effective amount of the derivatives of formula (I) defined above.

As shown by the $IC_{50}$ values reported in the examples, the compounds defined above constitute potent inhibitors of the DYRK1A kinase and, in this respect, are useful both as pharmacological tools for fundamental research and as therapeutic agents for the treatment of neurodegenerative diseases, in particular Alzheimer's disease and other tau pathologies, Pick's disease and trisomy 21.

The derivatives of formula I or the novel derivatives according to the invention in fact constitute tools for studying the functions of DYRK1A in various cell models, and the consequences of the expression thereof and of an abnormal activity. They constitute active ingredients of medicaments for countering the effects of the overexpression/abnormal activation of DYRK1A in the pathological conditions above.

During the production of medicaments, the active ingredients, used in therapeutically effective amounts, are mixed with the carriers that are pharmaceutically acceptable for the method of administration selected.

Thus for oral administration, the medicaments are prepared in the form of gel capsules, tablets, sugar-coated tablets, capsules, pills, drops, and the like. Such medicaments may contain from 1 to 100 mg of active ingredient per unit.

For injectable (intravenous, subcutaneous, intramuscular) administration, the medicaments are in the form of sterile or sterilizable solutions. The doses per unit intake may range from 1 to 50 mg of active ingredient. The daily dosage is chosen so as to obtain a final concentration of at most 100 μM of imidazolone analog or derivative in the blood of the patient treated.

According to yet another aspect, the present invention also relates to a method for synthesizing the imidazolone derivatives of formula I defined above.

This method is characterized in that it comprises the use of an arylidene thiohydantoin derivative corresponding to formula 3

(3)

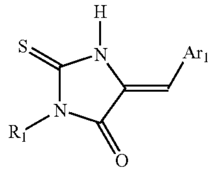

in which:

$R_1$, $R_2$ and $Ar_1$ are as defined above.

According to one embodiment aimed at preparing the imidazolone derivatives of formula I in which R═$R_2$S, the method of the invention comprises reacting a thiohydantoin derivative 3 with a halogenated derivative 3' of formula $R_2X$ (3')

with X═Cl, Br or I under conditions which make it possible to obtain an imidazolone derivative 4, according to scheme 4 below:

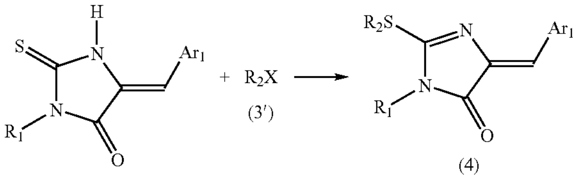

(3) (3') (4)

Advantageously, the reaction between the compounds 3 and 3' is carried out in an organic solvent, at a temperature of from 70 to 100° C., in particular of 80° C., in the presence of carbonate.

In order to more particularly obtain derivatives of formula (I) in which $R_2$ is an aryl radical, the method of the invention comprises reacting the thiohydantoin derivative 3 with an arylboronic acid 7' of formula $Ar_2B(OH)_2$ (7')

under conditions which give the derivatives of formula 8, according to scheme 1':

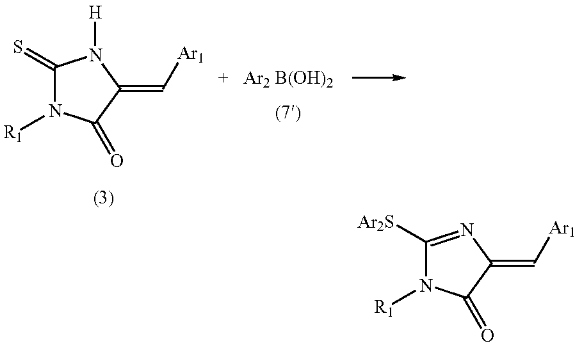

(3) (7') (8)

Satisfactory conditions correspond to a reaction, under microwave, of thioxohydantoin with boronic acid in the presence of $Cu(AcO)_2$, (with Ac=acetyl) and of phenanthroline in an organic solvent such as dichloroethane.

The mixture is irradiated for from 50 to 100 min, in particular from 60 to 90 min, at 70-90° C., in particular 80° C., with a maximum power of approximately 300 Watts.

According to one embodiment aimed at preparing the imidazolone derivatives of formula I in which R═$R_3$HN, the method of the invention comprises:

either reacting an imidazolone derivative as defined above 4 with an amine 4' of formula $R_3$—$NH_2$ (4')

under conditions which make it possible to obtain the imidazolone derivative 5 of formula and according to scheme 2 below:

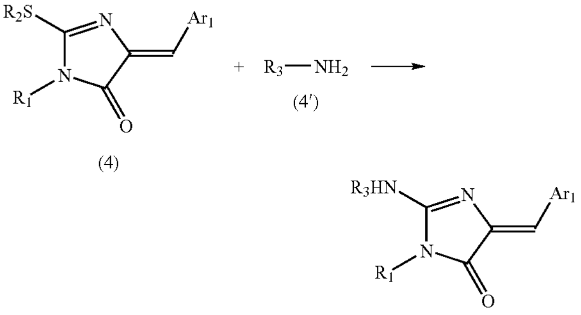

(4) (4') (5)

or reacting a hydantoin derivative 3 as defined above with an amine 4', according to scheme 3 below:

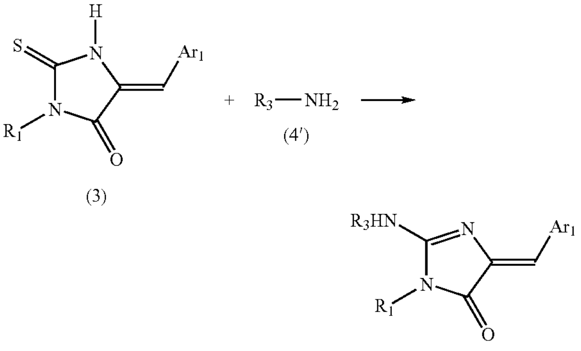

(3) (4') (5)

Preferably, the reaction according to scheme 3 is carried out in an oil bath and a microwave. In the procedure with the oil bath, the reaction mixture is heated to a temperature below the boiling point of the amine. When the procedure is carried out under microwave, the mixture is advantageously irradiated for from 10 to 100 minutes at an appropriate temperature and power.

The reaction according to scheme 3 is advantageously carried out in a solvent such as methanol in the presence of hydroperoxide.

According to one embodiment aimed at preparing the imidazolone derivatives of formula I in which R═$R_4$ COHN, the method of the invention comprises reacting an imidazolone derivative 5 of formula

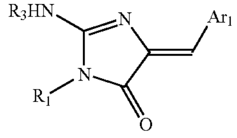

(5)

with an acid chloride 5' of formula $R_4COCl$ (5')

under conditions which make it possible to obtain an imidazolone derivative 6, according to scheme 4 below:

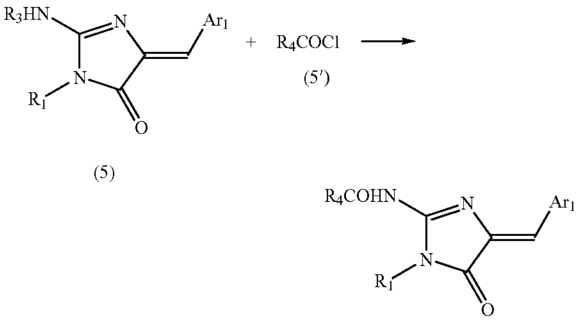

(5) (5') (6)

The substituents in these various formulae are as defined above.

Appropriate conditions for carrying out the reaction between these derivatives comprise the addition of triethylamine, and then of the acid chloride (5') to a solution, in an organic solvent such as THF, of the imidazolone derivative 5.

This reaction is advantageously carried out at a temperature of the order of 20 to 25° C.

In order to prepare the imidazolone derivatives of formula I in which R=$Ar_2$, the method of the invention comprises reacting a thiohydantoin derivative of formula 3 with a boronic acid 7'

$Ar_2B(OH)_2$ (7')

under conditions which make it possible to obtain an imidazolone derivative 7, according to scheme 5 below:

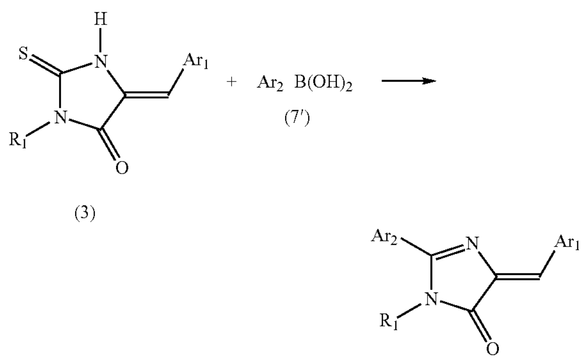

(3) (7') (7)

This reaction is advantageously carried out in the presence of a catalyst such as $Pd(PPh_3)_4$ and of CuTC (Copper Thiophene Carboxylate) in an anhydrous organic solvent such as anhydrous THF. This reaction is advantageously carried out at a temperature of the order of 55 to 65° C.

More particularly preferably, the thiohydantoin derivative 3 is obtained by reacting a thiohydantoin derivative of formula 2

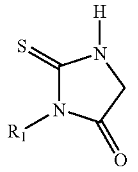

(2)

with an aldimine derivative of formula 2'

$Ar_1$-CH=N-alk (2')

the substituents being as defined above and "alk" representing a $C_3$-$C_5$ alkyl radical, according to scheme 6 below:

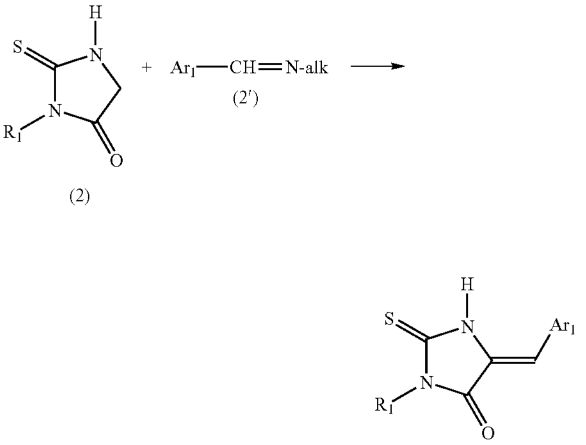

(2) (2') (3)

Advantageously, the reaction is carried out in an oil bath or under microwave.

In the oil bath procedure, the reactants are added to an organic solvent and the reaction mixture is brought to reflux. A viscous oil which crystallizes rapidly is recovered after filtration and purified if desired.

Among the appropriate organic solvents, mention will be made of acetonitrile.

In the microwave procedure, the mixture of thiohydantoin of formula 2 and of aldimine of formula 2' is placed in the microwave reactor, inserted into a microwave oven, where the mixture is irradiated, and then, at the end of the reaction and after a return to ambient temperature, the reaction product is recovered.

Appropriate conditions comprise a treatment of approximately 1 h at 70-100° C., in particular 80° C., with a maximum power of 80-100 Watts, more especially of 90 Watts.

The aldimine 2' is obtained, for example, starting from an aldehyde 2" $Ar_1$—CH═O and from propylamine 2''' $CH_3$—$(CH_2)_2$—$NH_2$. This reaction is advantageously carried out in a microwave reactor at a power of 300 Watts for example at 20-80° C., in particular 25 to 60° C., for 2 to 5 minutes, in particular 3 minutes, and then at 60-80° C. at a reduced power of the order of 10 to 30%, in particular 20%.

The thiohydantoin derivative 2 is preferably obtained by reacting methyl glycinate hydrochloride 1

$$CH_3O_2C—CH_2—NH_2,HCl \quad (1)$$

with an isothiocyanate 1' of formula $$R_1—N═C═S \quad (1')$$

according to scheme 7 below:

$$\underset{(1)}{CH_3O_2C—CH_2—NH_2\text{ , HCl}} \quad + \quad \underset{(1')}{R_1—N═C═S} \longrightarrow$$

-continued

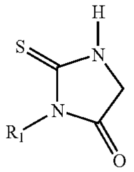

(2)

Satisfactory reaction conditions comprise reacting 1 and 1' in the presence of triethylamine, in a solvent such as ether, at reflux.

The intermediate compounds in these various operational stages are novel and, in this respect, are also part of the field of the invention.

Other characteristics and advantages of the invention are given in the following exemplary embodiments of the invention relating to the synthesis of the imidazolone derivatives according to the invention.

By way of illustration, the experimental conditions for the reactions denoted A to H, summarized in FIG. 1, are reported in the experimental section which follows.

The $IC_{50}$ values in μM with respect to DYRK1A of compounds according to the invention are subsequently given in table 2 in the section relating to the assay of the DYRD1A kinase activity.

EXPERIMENTAL SECTION

TABLE 1
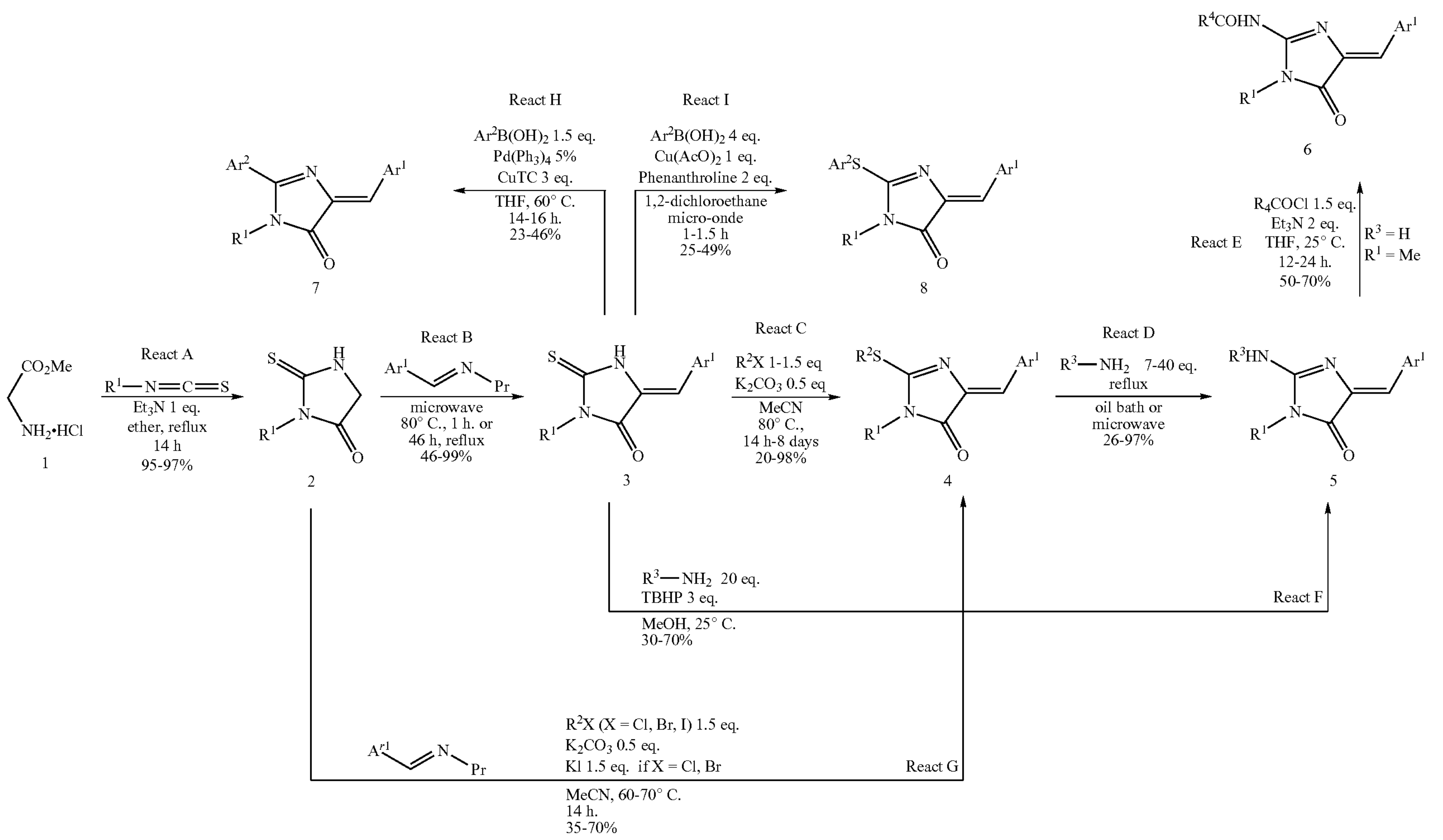

Reaction A:

React A

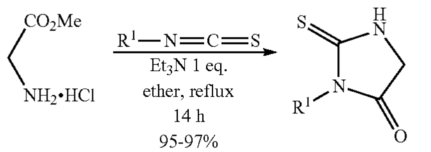

1 2

General Procedure:

A mixture constituted of 7 mmol of isothiocyanate ($R^1N{=}C{=}S$), 7 mmol (0.88 g) of methyl glycinate hydrochloride 1, and 7 mmol (0.97 ml) of triethylamine in 15 ml of ether is heated for 14 hours at the reflux of the solvent with vigorous magnetic stirring. After cooling of the reaction medium to ambient temperature, the solvent is eliminated under reduced pressure on a rotary evaporator. The triethylamine hydrochloride is eliminated by precipitation from ethyl acetate. After filtration through sintered glass with No. 4 porosity, the filtrate is concentrated on a rotary evaporator under reduced pressure and the expected product 2 is obtained. The latter is subsequently used without further purification.

Example of Compound 2

3-methyl-2-thioxoimidazolidin-4-one ($R^1$=Me)

Yield=95%, mp=170-172° C. $^1$H NMR (200 MHz, $CDCl_3$, TMS) δ: 3.27 (s, 3H, $NCH_3$); 4.11 (s, 2H, —$CH_2$—); 7.64 (broad s, 1H, NH). $^{13}$NMR (75 MHz, $CDCl_3$, TMS) δ: 27.6 ($NCH_3$); 48.6 (—$CH_2$—); 171.6 (C═O); 185.4 (C═S).

Reaction B:

React B

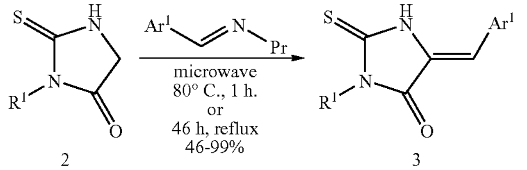

2 3

General Oil Bath Procedure:

Dichloromethane (20 ml), 6.9 mmol of thiohydantoin 2, and then 6.9 mmol of freshly distilled aldimine(*) are successively added to a round-bottomed flask equipped with a magnetic bar. The reaction mixture is subsequently brought to the reflux of dichloromethane and the reaction is monitored by thin layer chromatography on silica 60 F 254 (Merck). When the reaction is complete, the reaction medium is cooled to ambient temperature, and is then dried over anhydrous $MgSO_4$. After filtration through pleated paper, the filtrate solvent is eliminated by evaporation under reduced pressure and a viscous oil which crystallizes rapidly at ambient temperature is obtained. The purification is carried out either by recrystallization from pentane or, optionally, by chromatography on silica gel 60 F 254 (Merck) with an appropriate solvent.

General Microwave Procedure:

A mixture constituted of 10 mmol of thiohydantoin 2 and 10 mmol (1 equivalent) of aldimine(*) is placed in a cylindrical microwave reactor (Ø=4 cm). The reactor is then inserted into a Synthewave 402 microwave oven (trademark Prolabo, Merck-Eurolab group) fitted with a blade stirrer system. The mixture is irradiated for one hour at 80° C. (3-minute hold) with a maximum power of 90 Watts (Prolabo microwave). After a return to ambient temperature, the reaction mixture is then concentrated on a rotary evaporator. A solution of a chloroform/pentane mixture (1/2) is added to the evaporation residue. After trituration of this mixture, the insoluble solid is filtered through sintered glass with a No. 4 porosity and then dried under reduced pressure.

Example of Compound 3

(5Z)-5-(1,3-Benzodioxol-5-ylmethylene)-3-methyl-2-thioxoimidazolidin-4-one ($Ar^1$=1,3-benzodioxol-5-yl, $R^1$=Me)

Yield=87%. Yellow powder, mp=253-255° C. $^1$H NMR (300 MHz, DMSO-$d_6$) δ=3.18 (s, 3H, $NCH_3$); 6.09 (s, 2H, $OCH_2O$); 6.54 (s, 1H, C═CH); 6.96 (d, 1H, J=8.1 Hz, H-5); 7.27 (d, 1H, J=8.1 Hz, H-6); 7.45 (s, 1H, H-2); 12.22 (bs, 1H, NH). $^{13}$C NMR (75 MHz, DMSO-$d_6$) δ=27.6 ($NCH_3$); 102.1 ($OCH_2O$); 109.1 (C-5); 109.8 (C-2); 113.7 (C═CH); 125.1 (C═CH); 126.9 (C-6); 126.9 (C-1); 148.4 (C-4); 149.0 (C-3); 164.6 (C═O); 179.0 (C═S). HRMS, m/z: 262.0409 (calculated for $C_{12}H_{10}N_2O_3S$, 262.0412).

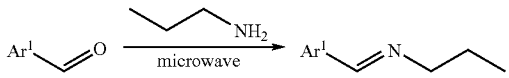

(*) General Procedure for the Synthesis of Aldimines:

20 mmol of aldehyde and 40 mmol (3.28 ml) of propylamine are successively weighed out into a quartz reactor. This reaction medium is heated in the Synthewave 402 microwave reactor ($P_{max}$=300 W, trademark Prolabo, Merck-Eurolab group) according to the following programming (from 25 to 60° C. for 3 minutes then at 60° C. for 30 minutes with a power of 20%). The excess propylamine is eliminated on a rotary evaporator under partial vacuum and then the evaporation residue (solid state) is solubilized in dichloromethane (10 ml/g of product); the organic solution is then dried over $MgSO_4$, and filtered through filter paper. The filtrate is concentrated on a rotary evaporator under reduced pressure.

Aldimine Example

N-[(1,3)-benzodioxol-5-ylmethylene]-N-propylamine ($Ar^1$=1,3-benzodioxol-5-yl)

Yield=97%. Yellow powder. $^1$H NMR (200 MHz, $CDCl_3$) δ: 0.90 (t, 3H, J=7.3 Hz, $NCH_2CH_2CH_3$); 1.64 (st, 2H, J=7.2 Hz, $NCH_2CH_2CH_3$); 3.47 (t, 2H, J=6.9 Hz, $NCH_2CH_2CH_3$); 5.90 (s, 2H, $OCH_2O$); 6.71 (d, 1H, J=7.9 Hz, H-5); 7.02 (dd, 1H, J=1.3; 7.9 Hz, H-6); 7.37 (d, 1H, J=1.4 Hz, H-2); 8.10 (s, 1H, N═CH). $^{13}$C NMR (75 MHz, $CDCl_3$) δ: 12.2 ($CH_3$); 24.5 ($CH_2CH_3$); 63.7 ($NCH_2$); 101.8 ($OCH_2O$); 107.0 (C-3); 108.4 (C-6); 124.5 (C-2); 131.6 (C-1); 148.6 (C-5); 150.0 (C-4); 160.3 (N═CH).

Reaction C:

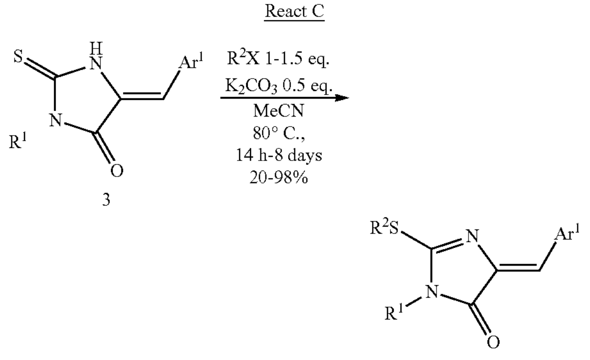

3

4

General Procedure:

The 5-arylidene thiohydantoin 3 (3.1 mmol, 1 eq.), 20 ml of acetonitrile, the halogenated derivative $R^2X$ with X═Cl, Br or I (3.1 mmol, 1 eq.) and 0.21 g of $K_2CO_3$ (1.5 mmol, 0.5 eq.) are successively added to a round-bottomed flask. The reaction mixture is heated at 80° C. for 14 hours with vigorous magnetic stirring. After cooling to ambient temperature, the acetonitrile is eliminated on a rotary evaporator under reduced pressure. 20 ml of ether are added to the crude reaction medium. After filtration of the insoluble inorganic products, under a partial vacuum, through sintered glass with a no. 4 porosity, the filtrate is dried over magnesium sulfate and then filtered through pleated paper. The filtrate solvent is eliminated on a rotary evaporator under reduced pressure and the expected imidazolone 4 is obtained in the form of a powder.

Example of Compound 4

[(Z)-(4-Benzo[1,3]dioxol-5-ylmethylene-1-methyl-5-oxo-4,5-dihydro-1H-imidazol-2-ylsulfanyl)]acetate ($Ar^1$=1,3-benzodioxol-5-yl, $R^1$=Me, $R^2$═$CH_2CO_2Et$)

Yield=92%. Yellow powder, mp=172-174° C. $^1H$ NMR (300 MHz, $CDCl_3$) δ: 1.26 (t, 3H, J=7.1 Hz, $OCH_2CH_3$); 3.12 (s, 3H, NMe); 4.02 (s, 2H, $SCH_2$); 4.23 (q, 2H, J=7.1 Hz, $OCH_2CH_3$); 5.96 (s, 2H, $OCH_2O$); 6.80 (d, 1H, J=8.1 Hz); 6.84 (s, 1H, ═CH); 7.52 (dd, 1H, J 8.1; 1.3 Hz); 7.96 (d, 1H, J=1.3 Hz). $^{13}C$ NMR (75 MHz, $CDCl_3$) δ: 14.1 (qm, J=128 Hz, $OCH_2CH_3$); 26.6 (q, 144 Hz, NMe); 32.9 (t, J=144 Hz, $SCH_2$); 62.3 (tq, J 148; 4.6 Hz, $OCH_2$); 101.5 (t, J=174 Hz, $OCH_2O$); 108.4 (d, J=165 Hz); 110.8 (dt, J 168; 6.9 Hz); 124.6 (dt, J 156; 4.1 Hz); 128.4 (dt, J 162; 6.0 Hz); 128.9 (d, J=7.6 Hz); 136.6 (s); 148.0 (m, ═C—O); 149.3 (m, ═C—O); 162.0 (m, C-2); 168.0 (m, C═O($CO_2Et$)); 169.7 (m, C-4). HRMS, m/z: 348.0791 (calc. for $C_{16}F_{16}N_2O_5S$: 348.0780).

Reaction D:

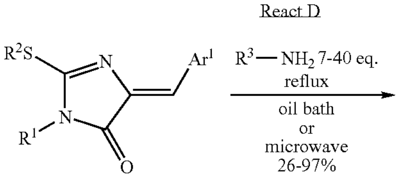

4

-continued

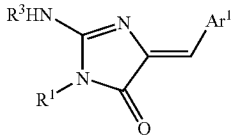

5

Microwave Procedure:

A mixture constituted of (5Z)-5-arylidene-2-alkylthio-3,5-dihydroimidazol-4-one 4 (4 mmol, 1 eq.) and of 5-20 mmol of aminoalcohol $R^3$—$NH_2$ (1.5 to 5 equivalents) is placed in a cylindrical microwave reactor (Ø=4 cm). The reactor is then inserted into the Synthewave 402 microwave oven (trademark Prolabo, Merck-Eurolab group) fitted with a blade stirrer system. The mixture is irradiated for from 15 minutes to 90 minutes at an appropriate temperature and an appropriate power. After a return to ambient temperature, the reaction mixture is then concentrated on a rotary evaporator. Ethanol (1 ml/g of product) is added to the evaporation residue. After trituration of the mixture from ethanol, the insoluble solid is filtered off through sintered glass with a no. 4 porosity and then dried under reduced pressure. The latter is optionally recrystallized from ethanol.

Oil Bath Procedure:

A suspension constituted of (5Z)-5-arylidene-2-alkylthio-3,5-dihydroimidazol-4-one 4 (4 mmol, 1 eq.) and of aliphatic amine (40 mmol, 10 eq.) is mixed with vigorous magnetic stirring and heated at a temperature 10° C. below the boiling point of this amine ($T_{exp}$.=$Bp_{amine}$−10° C.) for 3 to 7 days. After a return to ambient temperature, the volatile products are eliminated under reduced pressure and ether (~10 ml) is added to the reaction medium. Next, the products that are insoluble in ether are collected by filtration through sintered glass with a no. 4 porosity. The residual solvent of the compound 5 is eliminated under a partial vacuum in a desiccator for two hours, and the expected 2-aminoimidazolone 5 is obtained in the form of a yellow powder.

Example of 2-aminoimidazolone 5

(5Z)-5-Benzo[1,3]dioxol-5-ylmethylene-3-methyl-2-propylamino-3,5-dihydroimidazol-4-one ($Ar^1$=1,3-benzodioxol-5-yl, $R^1$=Me, $R^3$═$CH_2CH_2CH_3$)

Yield: 48%. Yellow powder, mp=190-192° C. $^1H$ NMR (300 MHz, $CDCl_3$) δ 1.02 (t, 3H, J=7.4 Hz); 1.74 (sext, 2H, J=7.3 Hz, $NHCH_2CH_2$); 3.11 (s, 3H, NMe); 3.54 (t, 2H, J=6.2 Hz, $NHCH_2C_2H_5$); 4.95 (bs, 1H, NH); 5.98 (s, 2H); 6.62 (s, 1H, ═CH); 6.81 (d, 1H, J=8.1 Hz); 7.34 (dd, 1H, J 8.1; 1.4 Hz); 7.99 (d, 1H, J=1.2 Hz). $^{13}C$ NMR (75 MHz, $CDCl_3$) δ 11.5 (qt, J 126; 4.0 Hz, $NHC_2H_4Me$); 22.8 (tq, J 135; 3.7 Hz, $NHCH_2CH_2$); 25.2 (q, J 140 Hz, NMe); 43.7 (tq, J 122; 7.0 Hz, $NHCH_2$); 101.1 (t, J=173 Hz, C-7'); 108.4 (d, J 164 Hz, C-2'); 110.3 (dt, J 166; 7.1 Hz, C-6); 116.8 (dt, J 157; 3.5 Hz); 126.1 (dt, J 163; 6.2 Hz, C-6'); 130.2 (d, J 7.8 Hz, C-5'); 138.1 (s, C-5); 147.6 (m, C-3'); 147.7 (m, C-4'); 157.2 (m, C-4); 170.4 (sm, C-2). HRMS, m/z: 287.1279 (calc. for $C_{15}H_{17}N_3O_3$: 287.1270).

Reaction E:

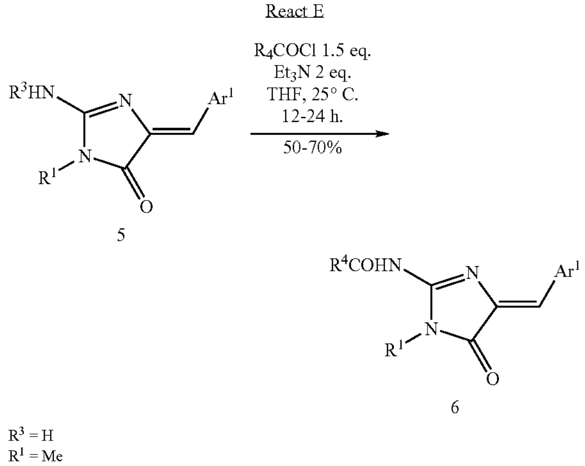

General Procedure:

Triethylamine (2 equiv.) and then acid chloride (1.5 equiv.) are added, at 0° C., to a solution of 0.2 mmol of 2-aminoimidazolone 5 ($R^3$=H, $R^1$=Me) in THF (2 ml). The reaction mixture is stirred at 25° C. for 12 h. The solution is then evaporated under reduced pressure and the residue is purified by flash chromatography on silica gel using a mixture of EtOAc/cyclohexane (9/1) as eluant.

Example of Compound 6

N-[(4Z)-4-Benzo[1,3]dioxol-5-ylmethylene-1-methyl-5-oxo-4,5-dihydro-1H-imidazol-2-yl]-2,2-dimethylpropanamide ($Ar^1$=1,3-benzodioxol-5-yl, $R^1$=Me, $R_4$=C($CH_3$)$_3$)

Yield: 50%. Yellow powder, mp=145-147° C. $^1$H NMR (300 MHz, $CDCl_3$): δ=1.28 (s, C($CH_3$)$_3$, 9H), 3.24 (s, $CH_3$, 3H), 6.05 (s, $OCH_2O$, 2H), 6.76 (s, =CH, 1H), 6.92 (d, J=8.0 Hz, $H_{ar}$, 1H), 6.93 (s, $H_{ar}$, 1H), 7.01 (d, J=8.0 Hz, $H_{ar}$, 1H). $^{13}$C NMR (75 MHz, $CDCl_3$): δ=25.6 (C($CH_3$)$_3$), 26.7 (C($CH_3$)$_3$), 39.7 ($NCH_3$), 101.6 ($OCH_2O$), 108.5, 111.2, 128.1, 129.1, 142.5, 146.5, 149.7, 161.8, 171.2, 179.1. HRMS, m/z=329.1377 (calculated for $C_{17}H_{19}N_3O_4$ 329.1375).

Reaction F:

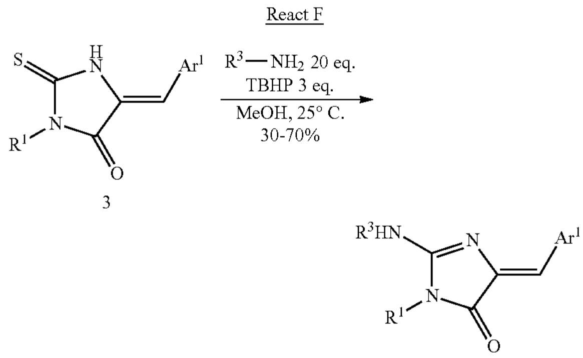

General Procedure:

3 equivalents of tert-butyl hydroperoxide TBHP (aqueous solution at 70%) and then 20 equivalents of amine are added to a solution of 3 (0.80 mmol) in MeOH (20 ml). The reaction mixture is stirred at 25° C. for three days. The solution is then evaporated under reduced pressure and the residue is purified by flash chromatography on silica gel using a mixture of $CH_2Cl_2$/MeOH (94/6) as eluant.

Example of Compound 5

(5Z)-5-Benzo[1,3]dioxol-5-ylmethylene-2-ethylamino-3,5-dihydro-4H-imidazol-4-one ($Ar^1$=1,3-benzodioxol-5-yl, $R^3$=Et, $R^1$=H)

Yield=40%. Yellow powder, mp=222-224° C. $^1$H NMR (300 MHz, DMSO-$d_6$): δ=1.17 (t, J=6.9 Hz, $CH_3$, 3H), 3.34 (m, $CH_2$, 2H), 6.02 (s, $OCH_2O$, 2H), 6.23 (s, =CH, 1H), 6.90 (d, J=8.1 Hz, $H_{ar}$, 1H), 7.20 (br.s, NH, 1H), 7.38 (d, J=8.1 Hz, $H_{ar}$, 1H), 7.93 (s, $H_{ar}$, 1H), 10.68 (br.s, NH, 1H). $^{13}$C NMR (75 MHz, DMSO-$d_6$): δ=15.5 ($CH_3$), 36.4 ($NHCH_2$), 101.4 ($OCH_2O$), 108.7, 109.8, 125.3, 131.0, 140.6, 146.9, 147.6, 160.2, 174.5. HRMS, m/z=259.0959 (calculated for $C_{13}H_{13}N_3O_3$ 259.0957).

Reaction G:

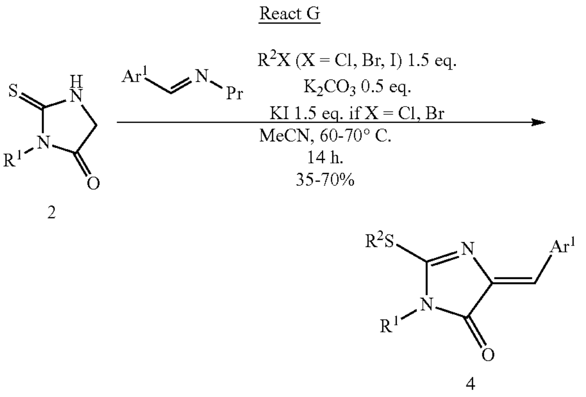

General Procedure:

A suspension constituted of 5 mmol of aldimine $Ar^1CH$=N—Pr, 5 mmol of thiohydantoin 2 ($R^1$=Me, Bu, Ph), 7.5 mmol of haloalkane $R^2X$, 0.345 g (2.5 mmol) of potassium carbonate and, optionally, 1.25 g (7.5 mmol) of KI (if use is made of a halogenated derivative $R^2X$ with X=Br or Cl) in 10 ml of acetonitrile is heated for 14 hours at a temperature close to the boiling point of the haloalkane $R^2X$ ($T_{exp.}$=$Bp_{R2X}$−10° C.). The reaction solvent is then eliminated on a rotary evaporator under reduced pressure. The solid obtained after evaporation is triturated with dichloromethane (10 ml/g of product) and then the insoluble inorganic salts are eliminated by filtration through paper. After evaporation of the filtrate, the crude reaction medium is treated (1 g/10 ml) with a mixture of pentane/ethanol (1/1). The expected product 4 precipitates, and is then collected through sintered glass with a no. 4 porosity and dried in a desiccator under a partial vacuum.

Example of Compound 4

(5Z)-5-(1,3-benzodioxol-5-ylmethylene)-3-methyl-2-(ethyl thio)-3,5-dihydro-4H-imidazol-4-one ($Ar^1$=1,3-benzodioxol-5-yl, $R^1$=Me, $R^3$=Et)

Yield=92%. Orangey-yellow powder, mp=152-154° C. $^1$H NMR (300 MHz, $CDCl_3$) δ: 1.55 (t, 3H, J=7.4 Hz, $SCH_2CH_3$); 3.17 (S, 3H, NCH3); 3.40 (q, 2H, J=7.4 Hz, $SCH_2CH_3$); 6.00 (s, 2H, $OCH_2O$); 6.82 (d, 1H, J=8.1 Hz, H-5); 6.83 (s, 1H, =CH); 7.37 (dd, 1H, J=8.1; 1.0 Hz, H-6); 8.05 (s, 1H, H-2). $^{13}C$ NMR (75 MHz, $CDCl_3$) δ: 14.7 ($SCH_2CH_3$); 25.6 ($SCH_2CH_3$); 26.9 ($NCH_3$); 101.8 ($OCH_2O$); 108.8 (C-5); 111.2 (C-2); 124.0 (=CH); 128.4 (C-6); 129.5 (C-1); 137.5 (NC=C); 148.3 (C-4); 149.5 (C-3); 164.1 (C—S); 170.3 (C=O). HRMS, m/z=290.0730 found (calculated for $C_{14}H_{14}N_2O_3S$: 290.0725, $M^{++}$).

Reaction H:

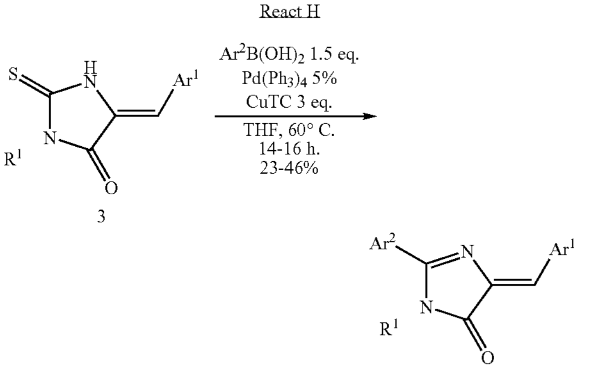

7

General Procedure:

A solution constituted of (5Z)-5-arylidene thiohydantoin 3 (1 equivalent), of boronic acid $Ar^2B(OH)_2$ (1.5 equivalents), of $Pd(PPh_3)_4$ (5 mol %) and of CuTC (3 equivalents) in anhydrous THF (0.06 M) is introduced into a Schlenk tube. The reaction mixture is brought to the reflux of THF overnight with vigorous magnetic stirring. After a return to ambient temperature, the reaction medium is extracted with dichloromethane (twice). The organic phase is washed with a solution of sodium hydrogen sulfate (1M), and then with a saturated solution of sodium chloride and, finally, with a solution of sodium hydrogen carbonate (1M). The organic phase is dried over $MgSO_4$ and filtered through paper, and the filtrate is concentrated on a rotary evaporator under vacuum. The evaporation residue is solubilized under hot conditions in diethyl ether. After cooling, the crystals are collected by filtration through sintered glass with a no. 4 porosity, under a partial vacuum, and then purified by silica gel chromatography with a cyclohexane/ethyl acetate mixture (70/30) as eluant. The chromatography fraction is then concentrated on a rotary evaporator and dried under a partial vacuum, resulting in the expected product 7.

Example of Compound 7

(5Z)-5-(1,3-Benzodioxol-5-ylmethylene)-3-methyl-2-phenyl-3,5-dihydro-4H-imidazol-4-one ($Ar^1$=1,3-benzodioxol-5-yl, $R^1$=Me, $Ar^2$=$C_6H_5$)

Yield=46%. Yellow powder, mp=209-211° C. $^1H$ NMR (300 MHz, $CDCl_3$): δ=3.35 (s, 3H, NCHO; 6.01 (s, 2H, $OCH_2O$); 6.84 (d, 1H, J=8.1 Hz, H-5'); 7.16 (s, 1H, C=CH); 7.47 (dd, 1H, J=8.1 Hz, J=1.2 Hz, H-6'); 7.53 (m, 3H, H-3", H-4"); 7.84 (dd, 2H, J=7.4 Hz, J=2.2 Hz, H-2"); 8.14 (d, 1H, J=1.2 Hz, H-2'). $^{13}C$ NMR (75 MHz, $CDCl_3$) δ=29.1 (NMe); 101.5 ($OCH_2O$); 108.5 (C-5'); 111.5 (C-2'); 128.7 (C-2"); 128.8 (C-3"); 128.8 (C=CH); 129.0 (C-6'); 129.4 (C-1"); 131.4 (C-4"); 137.5 (C=CH); 137.5 (C-1'); 148.1 (C-3'); 149.7 (C-4'); 161.4 (C=N); 171.6 (C=O). HRMS, m/z: 306.0995 (calculated for $C_{18}H_{14}N_2O_3$: 306.10044).

Reaction I:

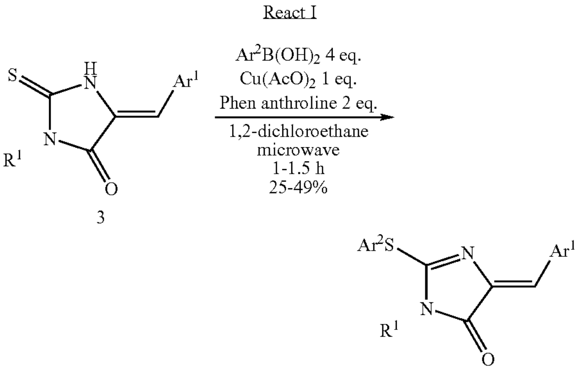

8

General Procedure:

0.4 mmol of (5Z)-5-arylidene thiohydantoin 3, 1.6 mmol (4 equivalents) of boronic acid, 0.4 mmol (1 equivalent) of $CuOAc_2$, 0.8 mmol (2 equivalents) of phenanthroline and 4 ml of dichloroethane are placed in a cylindrical microwave reactor (Ø=2.8 cm). This reactor is then inserted into the microwave oven fitted with a blade stirrer system. The mixture is irradiated for 60 to 90 minutes at 80° C. (2-minute hold) with a maximum power of 300 Watts (Prolabo microwave). After cooling to ambient temperature, the reaction mixture is then concentrated on a rotary evaporator under a partial vacuum. The expected product 8 is purified on alumina gel, elution being carried out with a pentane/ethyl acetate mixture (85/15), followed by washing with pentane.

Example of Compound 8

(5Z)-5-(1,3-Benzodioxol-5-ylmethylene)-3-methyl-2-(phenylthio)-3,5-dihydro-4H-imidazol-4-one ($Ar^1$=1,3-benzodioxol-5-yl, $R^1$=Me, $Ar^2$=$C_6H_5$)

Yield: 49%. Yellow powder, mp=171-173° C. $^1H$ NMR (300 MHz, Acetone-$d_6$): δ=3.22 (s, 3H, $NCH_3$); 6.03 (s, 2H, $OCH_2O$); 6.77 (s, 1H, C=CH); 6.82 (d, 1H, J=8.1 Hz, H-5'); 7.36 (dd, 1H, J=8.1 Hz, J=1.2 Hz, H-6'); 7.56 (d, 1H, J=1.7 Hz, H-2'); 7.58 (d, 2H, J=1.7 Hz, H-2"); 7.78 (m, 2H, H-3"); 7.83 (d, 1H, J=1.3 Hz, H-4"). $^{13}C$ NMR (75 MHz, DMSO-$d_6$) δ=26.6 (NMe); 101.5 ($OCH_2O$); 108.3 (C-5'); 109.9 (C-2'); 123.4 (C=CH); 125.1 (C-1"); 128.3 (C-6'); 128.4 (C-1'); 129.4 (C-2"); 130.0 (C-4"); 134.8 (C-3"); 136.5 (C=CH); 147.5 (C-4'); 148.9 (C-3'); 162.8 (C=N); 168.5 (C=O). HRMS, m/z: 338.0738 (calculated for $C_{18}H_{14}N_2O_3S$: 338.07251).

Assaying of the Kinase Activity of DYRK1A

Biochemical Reagents

Sodium ortho-vanadate, EGTA, Mops, β-glycerophosphate, phenylphosphate, dithiothreitol (DTT), glutathione-agarose, glutathione, nitrophenylphosphate and myelin basic protein were obtained from Sigma Chemicals. [γ-$^{33}$P]-ATP comes from Amersham.

Preparation of the DYRK1A Kinase and Enzyme Assay for the Activity Thereof

Rat recombinant DYRK1A was expressed in *E. coli* as a GST fusion protein. It was purified by affinity chromatography on beads of immobilized glutathione (elution with free glutathione). The kinase activity was assayed in buffer C (60 mM β-glycerophosphate, 15 mM p-nitrophenylphosphate, 25 mM Mops (pH 7.2), 5 mM EGTA, 15 mM $MgCl_2$, 1 mM DTT, 1 mM sodium vanadate, 1 mM phenylphosphate), with 1 mg of myelin basic protein/ml, in the presence of 15 μM [γ-$^{33}$P]-ATP (3.000 Ci/mmol; 10 mCi/ml) in a final volume of 30 μL. After incubation at 30° C. for 30 min, 25-μL aliquots of supernatant were spotted onto Whatman P81 phosphocellulose filters and the filters were washed five times in a solution of phosphoric acid (10 ml/L water). The radioactivity incorporated into the substrate, retained on the moist filters, was then counted in the presence of ACS scintillation fluid (Amersham). The control values were subtracted and the activities were expressed as % of the maximum value, i.e. the value obtained in the absence of inhibitors. The $IC_{50}$ values were calculated from dose-response curves and are given in μM.

The results are given in table 2 hereinafter:

TABLE 2

3

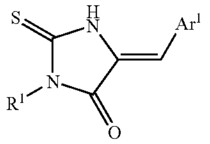

| Molecule Reference | $IC_{50}$ DYRK1A (μM) | $R^1$ | $Ar^1$ | Reaction used |
|---|---|---|---|---|
| JR361 | >10 | n-Bu | 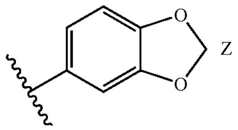 [SMILES: *c1ccc2c(c1)OCO2] | B |
| JR370 | >10 | Ph | 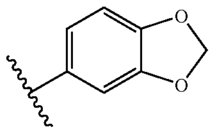 [SMILES: *c1ccc2c(c1)OCO2] | B |
| FC071 | 2.6 | H | 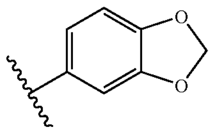 [SMILES: *c1ccc2c(c1)OCO2] | B |
| ST341 | >10 | Me | 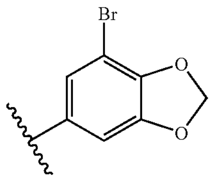 [SMILES: *c1cc(Br)c2c(c1)OCO2] | B |

TABLE 2-continued

3

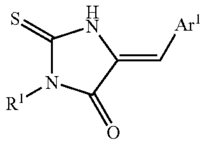

| Molecule Reference | $IC_{50}$ DYRK1A (μM) | $R^1$ | $Ar^1$ | Reaction used |
|---|---|---|---|---|
| ST279 | >10 | H | 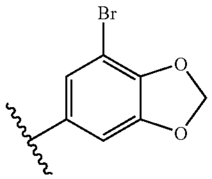 [SMILES: *c1cc(Br)c2c(c1)OCO2] | B |
| ST089 | >10 | Me | 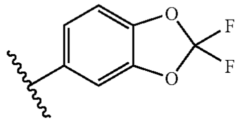 [SMILES: *c1ccc2c(c1)OC(F)(F)O2] | B |
| ST076 | >10 | Me | 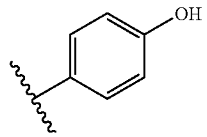 | B |
| ST169 | >10 | Me | 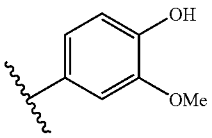 [SMILES: *c1ccc(O)c(OC)c1] | B |
| ST202 | >10 | H | 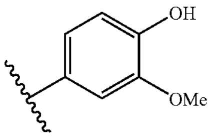 | B |
| ST227 | 66 | H | 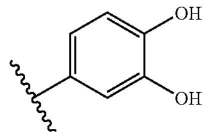 [SMILES: *c1ccc(O)c(O)c1] | B |
| ST229 | 65 | H | 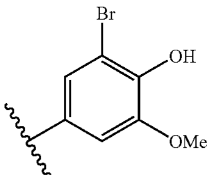 [SMILES: *c1cc(Br)c(O)c(OC)c1] | B |

TABLE 2-continued

3

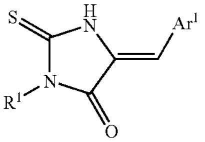

| Molecule Reference | $IC_{50}$ DYRK1A (μM) | $R^1$ | $Ar^1$ | Reaction used |
|---|---|---|---|---|
| ST197 | >10 | Me | 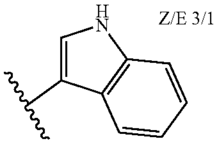 [SMILES: *c1c[nH]c2ccccc12] Z/E 3/1 | B |
| ST195 | >10 | H | 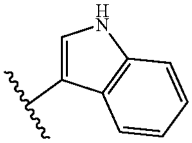 [SMILES: *c1c[nH]c2ccccc12] | B |

TABLE 2-continued

3

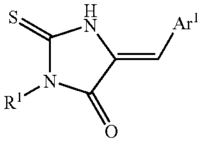

| Molecule Reference | $IC_{50}$ DYRK1A (μM) | $R^1$ | $Ar^1$ | Reaction used |
|---|---|---|---|---|
| ST223 | >10 | Me | 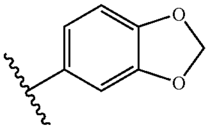 [SMILES: *c1ccc2c(c1)OCO2] | B |

References:

1: Microwave mediated solventless synthesis of new derivatives of marine alkaloid Leucettamine B.
Jean René Chérouvrier, François Carreaux, Jean Pierre Bazureau
Tetrahedron Letters 2002, 43, 3581-3584.

2: The isolation and synthesis of polyandrocarpamines A and B. Two new 2-aminoimidazolone compounds from the Fijian ascidian, *Polyandrocarpa* sp.
Rohan A. Davis, William Aalbersberg, Semisi Meo, Rosan Moreira da Rocha, Chris M. Ireland
Tetrahedron 2002, 58, 3263-3269.

4

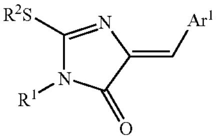

| Molecule reference | $IC_{50}$ DYRK1A (μM) | $R^1$ | $SR^2$ | $Ar^1$ | Reaction used |
|---|---|---|---|---|---|
| ST099 | 6.8 | Me | SMe | 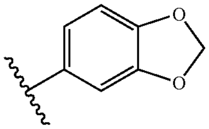 [SMILES: *c1ccc2c(c1)OCO2] | C |
| SB26 | 1.4 | Me | SEt | 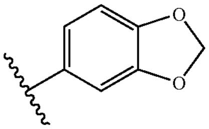 [SMILES: *c1ccc2c(c1)OCO2] | G |
| ST094 | 1.8 | Me | Sn-Pr | 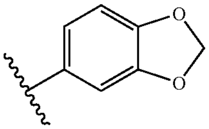 [SMILES: *c1ccc2c(c1)OCO2] | C |
| ST097 | 1.3 | Me | Si-Pr | 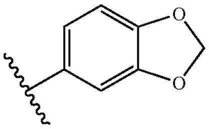 [SMILES: *c1ccc2c(c1)OCO2] | C |
| SB14 | 3.4 | Me | 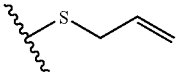 [SMILES: *SCC=C] | 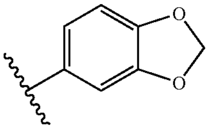 [SMILES: *c1ccc2c(c1)OCO2] | G |

-continued
| | | | | | |
|---|---|---|---|---|---|
| SB16 | 0.9 | Me | 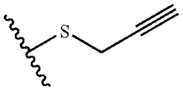 [SMILES: *SCC#C] | 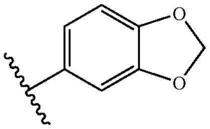 [SMILES: *c1ccc2c(c1)OCO2] | G |
| ST211 | 0.47 | Me | 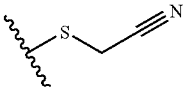 [SMILES: *SCC#N] | 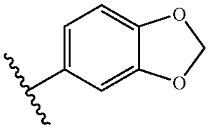 [SMILES: *c1ccc2c(c1)OCO2] | C |
| ST381 | 0.44 | Me | $SCH_2CH_2Cl$ | 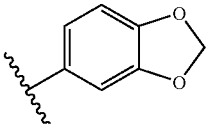 [SMILES: *c1ccc2c(c1)OCO2] | C |
| ST101 | 2.3 | Me | Sn-Bu | 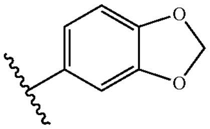 [SMILES: *c1ccc2c(c1)OCO2] | C |
| ST102 | 1.5 | Me | 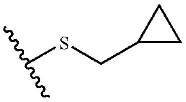 [SMILES: *SCC1CC1] | 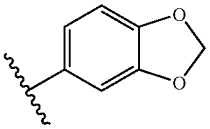 [SMILES: *c1ccc2c(c1)OCO2] | C |
| SA197 | 2.5 | Me | 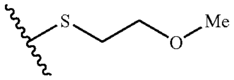 [SMILES: *SCCOC] | 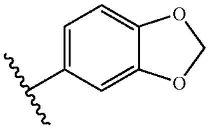 [SMILES: *c1ccc2c(c1)OCO2] | C |
| JR404 | 5.8 | Me | 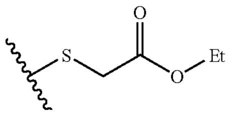 [SMILES: *SCC(=O)OCC] | 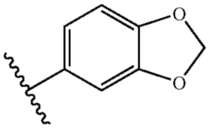 [SMILES: *c1ccc2c(c1)OCO2] | C |
| SB28 | 5.7 | Me | SBn | 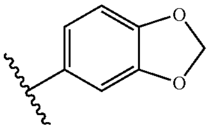 [SMILES: *c1ccc2c(c1)OCO2] | G |
| ST342 | >10 | Me | SEt | 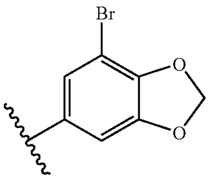 [SMILES: *c1cc(Br)c2c(c1)OCO2] | C |
| ST091 | >10 | Me | SEt | 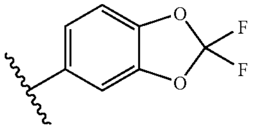 [SMILES: *c1ccc2c(c1)OC(F)(F)O2] | C |

-continued
| | | | | | |
|---|---|---|---|---|---|
| ST078 | 6.7 | Me | SMe | 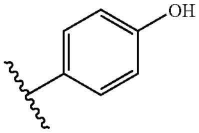 [SMILES: *c1ccc(O)cc1] | C |
| JR159 | >10 | Me | SMe | 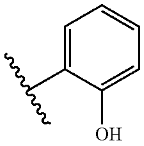 [SMILES: *c1ccccc1O] | C |
| ST170 | >10 | Me | SEt | 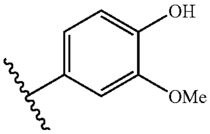 [SMILES: *c1ccc(O)c(OC)c1] | C |
| SB55 | >10 | Me | SEt | 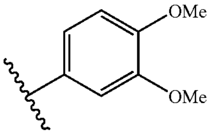 [SMILES: *c1ccc(OC)c(OC)c1] | G |
| JR161 | >10 | Me | SMe | 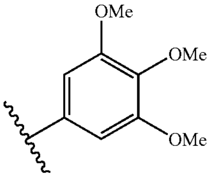 [SMILES: *c1cc(OC)c(OC)c(OC)c1] | C |
| SB56 | >10 | Me | SEt | 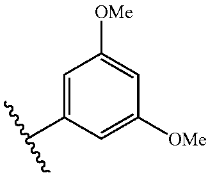 [SMILES: *c1cc(OC)cc(OC)c1] | G |
| JR158 | >10 | Me | SMe | 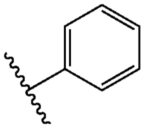 [SMILES: *c1ccccc1] | C |
| JR160 | >10 | Me | SMe | 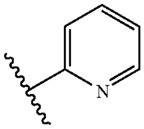 [SMILES: *c1ccccn1] | C |
| JR162 | >10 | Me | SMe | 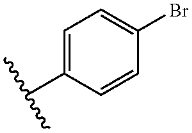 [SMILES: *c1ccc(Br)cc1] | C |
| FB08 | >10 | Me | SEt | 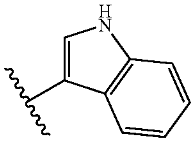 [SMILES: *c1c[nH]c2ccccc12] | C |

-continued
| | | | | | |
|---|---|---|---|---|---|
| FB14 | >10 | Me | Sn-Pr | 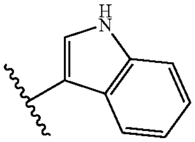 [SMILES: *c1c[nH]c2ccccc12] | C |
| FB17 | >10 | Me | Sn-Bu | 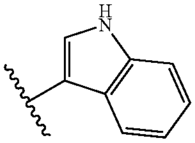 [SMILES: *c1c[nH]c2ccccc12] | C |
| JR448 | >10 | n-Bu | SMe | 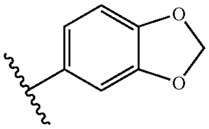 [SMILES: *c1ccc2c(c1)OCO2] | C |
| SB05 | >10 | n-Bu | SEt | 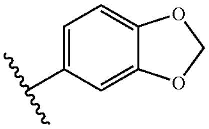 [SMILES: *c1ccc2c(c1)OCO2] | G |
| SB25 | >10 | n-Bu | 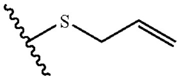 [SMILES: *SCC=C] | 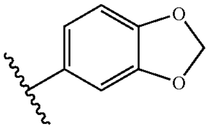 [SMILES: *c1ccc2c(c1)OCO2] | G |
| SB22 | >10 | n-Bu | 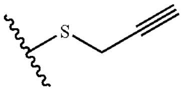 [SMILES: *SCC#C] | 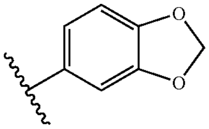 [SMILES: *c1ccc2c(c1)OCO2] | G |
| SB10 | >10 | n-Bu | SBn | 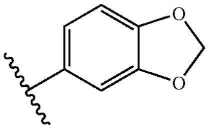 [SMILES: *c1ccc2c(c1)OCO2] | G |
| SB60 | >10 | n-Bu | 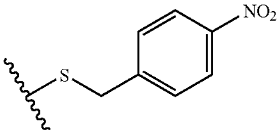 [SMILES: *SCc1ccc([N+](=O)[O-])cc1] | 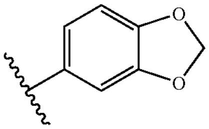 [SMILES: *c1ccc2c(c1)OCO2] | G |
| SB80 | >10 | n-Bu | SEt | 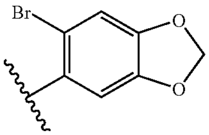 [SMILES: *c1cc2c(cc1Br)OCO2] | G |
| SB58 | >10 | n-Bu | SEt | 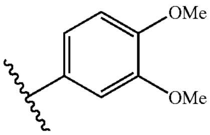 [SMILES: *c1ccc(OC)c(OC)c1] | G |
| JR411 | >10 | Ph | 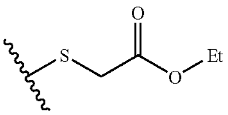 [SMILES: *SCC(=O)OCC] | 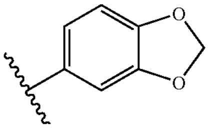 [SMILES: *c1ccc2c(c1)OCO2] | C |

-continued
| | | | | | |
|---|---|---|---|---|---|
| ST105 | 0.68 | H | SMe | 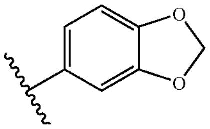 [SMILES: *c1ccc2c(c1)OCO2] | C |
| ST120 | 0.44 | H | SEt | 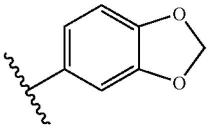 [SMILES: *c1ccc2c(c1)OCO2] | C |
| ST122 | 0.44 | H | Sn-Pr | 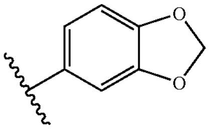 [SMILES: *c1ccc2c(c1)OCO2] | C |
| ST135 | 0.46 | H | Si-Pr | 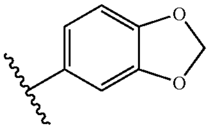 [SMILES: *c1ccc2c(c1)OCO2] | C |
| ST209 | 0.17 | H | 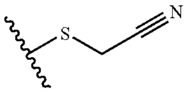 [SMILES: *SCC#N] | 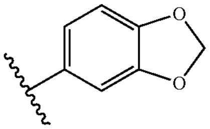 [SMILES: *c1ccc2c(c1)OCO2] | C |
| ST124 | 0.59 | H | Sn-Bu | 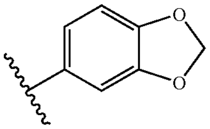 [SMILES: *c1ccc2c(c1)OCO2] | C |
| ST164 | 0.65 | H | 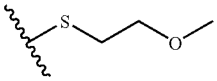 [SMILES: *SCCOC] | 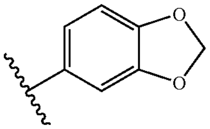 [SMILES: *c1ccc2c(c1)OCO2] | C |
| ST130 | 0.5 | H | 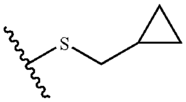 [SMILES: *SCC1CC1] | 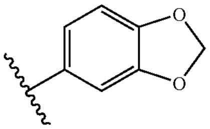 [SMILES: *c1ccc2c(c1)OCO2] | C |
| ST142 | 0.78 | H | 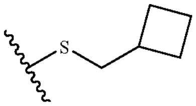 [SMILES: *SCC1CCC1] | 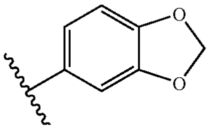 [SMILES: *c1ccc2c(c1)OCO2] | C |
| ST240 | 2.6 | H | SEt | 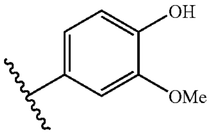 [SMILES: *c1ccc(O)c(OC)c1] | C |
| ST286 | >10 | H | SEt | 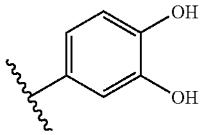 [SMILES: *c1ccc(O)c(O)c1] | C |

-continued
| | | | | | |
|---|---|---|---|---|---|
| ST280 | >10 | H | SEt | 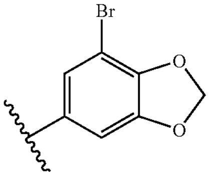 [SMILES: *c1cc(Br)c2c(c1)OCO2] | C |
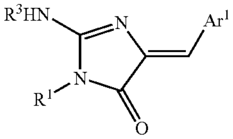
| Molecule reference | $IC_{50}$ DYRK1A (μM) | $R^1$ | $NHR^3$ | $Ar^1$ | Reaction used |
|---|---|---|---|---|---|
| FC077 | 4.7 | Me | $NH_2$ | 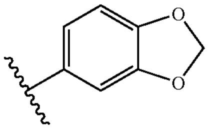 [SMILES: *c1ccc2c(c1)OCO2] | F |
| FC084 | 2.7 | Me | NHMe | 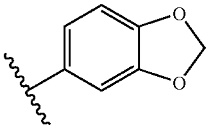 [SMILES: *c1ccc2c(c1)OCO2] | F |
| FC088 | 0.9 | Me | NHEt | 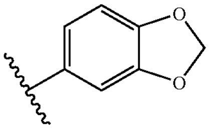 [SMILES: *c1ccc2c(c1)OCO2] | F |
| FCJR405 | 2.3 | Me | NHn-Pr | 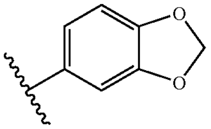 [SMILES: *c1ccc2c(c1)OCO2] | D Oil bath |
| FCJR232 | 1.3 | Me | NHi-Pr | 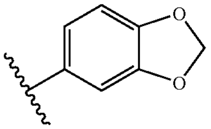 [SMILES: *c1ccc2c(c1)OCO2] | D Oil bath |
| FCFD13 | 1.6 | Me | 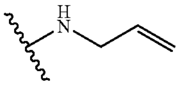 | 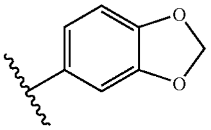 [SMILES: *c1ccc2c(c1)OCO2] | D Oil bath |
| MADE40 | 0.73 | Me | $NHCH_2CH_2OH$ | 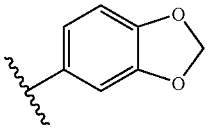 [SMILES: *c1ccc2c(c1)OCO2] | D Microwave |
| MADE26 | >10 | Me | 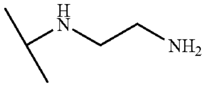 | 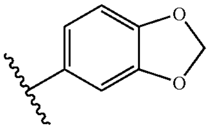 [SMILES: *c1ccc2c(c1)OCO2] | D Microwave |

-continued
| | | | | | |
|---|---|---|---|---|---|
| MADE47 | 0.79 | Me | 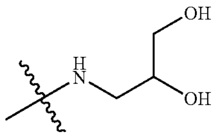 [SMILES: *NCC(O)CO] | 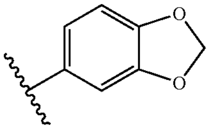 [SMILES: *c1ccc2c(c1)OCO2] | D Microwave |
| MADE24 | >10 | Me | 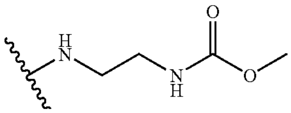 [SMILES: *NCCNC(=O)OC] | 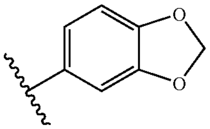 [SMILES: *c1ccc2c(c1)OCO2] | D Microwave |
| IA24 | >10 | Me | NHAc | 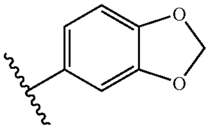 [SMILES: *c1ccc2c(c1)OCO2] | E |
| FCJR457 | 1.8 | Me | NHn-Bu | 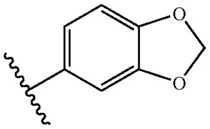 [SMILES: *c1ccc2c(c1)OCO2] | D Oil bath |
| FCFD24 | >10 | Me | NHi-Bu | 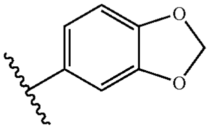 [SMILES: *c1ccc2c(c1)OCO2] | D Oil bath |
| FC107 | 0.98 | Me | 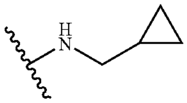 | 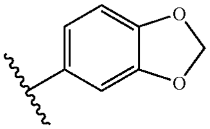 [SMILES: *c1ccc2c(c1)OCO2] | F |
| SA142 | 1.3 | Me | 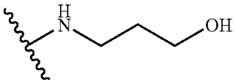 [SMILES: *NCCCO] | 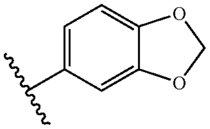 [SMILES: *c1ccc2c(c1)OCO2] | D Oil bath |
| FC103 | 1.2 | Me | 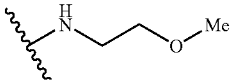 [SMILES: *NCCOC] | 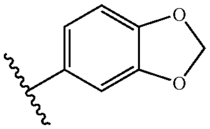 [SMILES: *c1ccc2c(c1)OCO2] | F |
| ST025 | 1.7 | Me | NHi-Am | 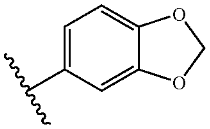 [SMILES: *c1ccc2c(c1)OCO2] | D Oil bath |
| MADE23 | 3 | Me | 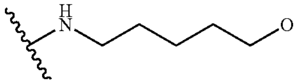 [SMILES: *NCCCCCO] | 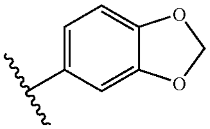 [SMILES: *c1ccc2c(c1)OCO2] | D Microwave |
| MADE10 | 1.4 | Me | 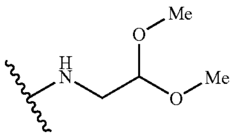 [SMILES: *NCC(OC)OC] | 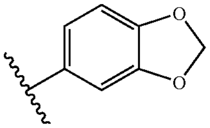 [SMILES: *c1ccc2c(c1)OCO2] | D Microwave |

-continued
| | | | | | |
|---|---|---|---|---|---|
| MADE9 | 0.69 | Me | 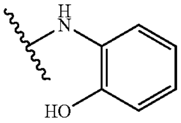 [SMILES: *Nc1ccccc1O] | 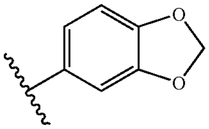 [SMILES: *c1ccc2c(c1)OCO2] | D Microwave |
| MADE32 | 0.4 | Me | $NHC_6H_5$ | 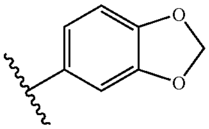 [SMILES: *c1ccc2c(c1)OCO2] | D Microwave |
| MADE8 | 0.38 | Me | 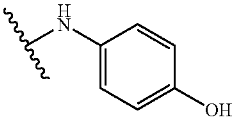 [SMILES: *Nc1ccc(O)cc1] | 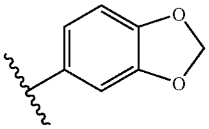 [SMILES: *c1ccc2c(c1)OCO2] | D Microwave |
| MADE33 | 0.94 | Me | 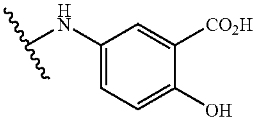 [SMILES: *Nc1ccc(O)c(C(=O)O)c1] | 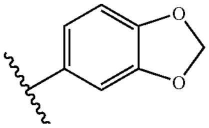 [SMILES: *c1ccc2c(c1)OCO2] | D Microwave |
| MADE30 | 0.37 | Me | 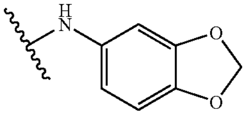 [SMILES: *Nc1ccc2c(c1)OCO2] | 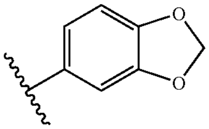 [SMILES: *c1ccc2c(c1)OCO2] | D Microwave |
| MADE29 | 0.19 | Me | 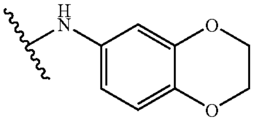 [SMILES: *Nc1ccc2c(c1)OCCO2] | 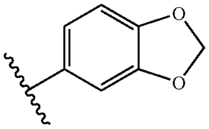 [SMILES: *c1ccc2c(c1)OCO2] | D Microwave |
| MADE39 | 0.27 | Me | 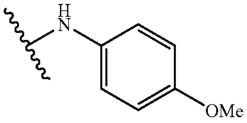 [SMILES: *Nc1ccc(OC)cc1] | 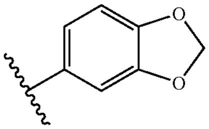 [SMILES: *c1ccc2c(c1)OCO2] | D Microwave |
| MADE37 | 0.23 | Me | 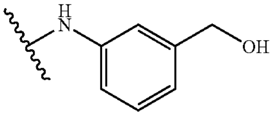 [SMILES: *Nc1cccc(CO)c1] | 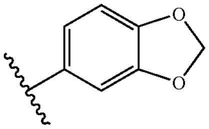 [SMILES: *c1ccc2c(c1)OCO2] | D Microwave |
| MADE36 | 0.26 | Me | 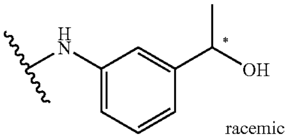 [SMILES: *Nc1cccc(C(C)O)c1] racemic | 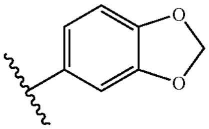 [SMILES: *c1ccc2c(c1)OCO2] | D Microwave |
| MADE42 | 0.43 | Me | 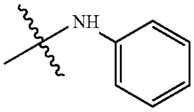 [SMILES: *Nc1ccccc1] | 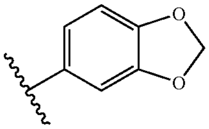 [SMILES: *c1ccc2c(c1)OCO2] | D Microwave |
| MADE35 | 0.42 | Me | 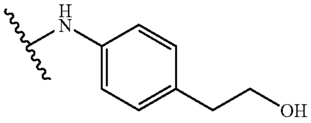 [SMILES: *Nc1ccc(CCO)cc1] | 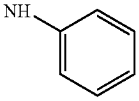 | D Microwave |

-continued
| | | | | | |
|---|---|---|---|---|---|
| MADE34 | 0.86 | Me | 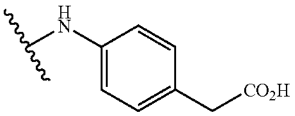 [SMILES: *Nc1ccc(CC(=O)O)cc1] | 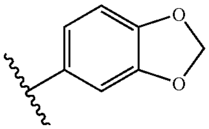 [SMILES: *c1ccc2c(c1)OCO2] | D Microwave |
| FC097 | 1.4 | Me | NHBn | 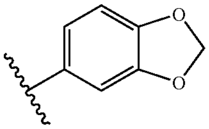 [SMILES: *c1ccc2c(c1)OCO2] | F |
| MADE12 | 4.6 | Me | 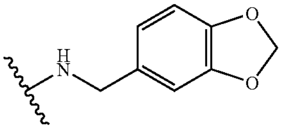 [SMILES: *NCc1ccc2c(c1)OCO2] | 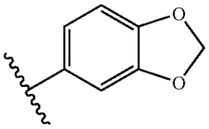 [SMILES: *c1ccc2c(c1)OCO2] | D Microwave |
6
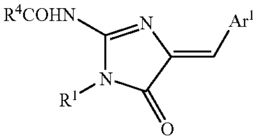
| Molecule reference | $IC_{50}$ DYRK1A (μM) | $R^1$ | $NHCOR^4$ | $Ar^1$ | Reaction used |
|---|---|---|---|---|---|
| IA32 | 15 | Me | 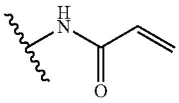 [SMILES: *NC(=O)C=C] | 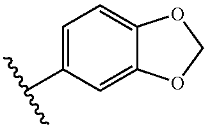 [SMILES: *c1ccc2c(c1)OCO2] | E |
| IA31 | 3.4 | Me | 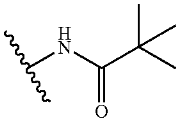 [SMILES: *NC(=O)C(C)(C)C] | 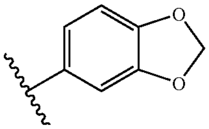 [SMILES: *c1ccc2c(c1)OCO2] | E |
| IA33 | >10 | Me | 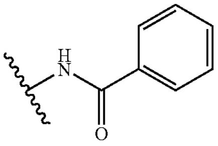 [SMILES: *NC(=O)c1ccccc1] | 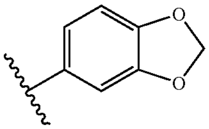 [SMILES: *c1ccc2c(c1)OCO2] | E |
| IA25 | >10 | Me | 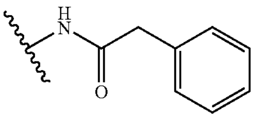 [SMILES: *NC(=O)Cc1ccccc1] | 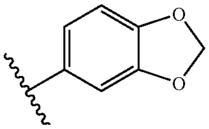 [SMILES: *c1ccc2c(c1)OCO2] | E |
| IA35 | >10 | Me | 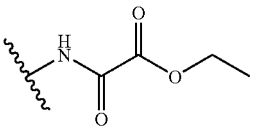 [SMILES: *NC(=O)C(=O)OCC] | 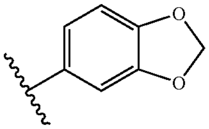 [SMILES: *c1ccc2c(c1)OCO2] | E |
5

-continued
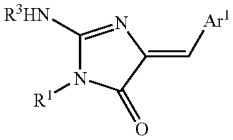
| Molecule reference | $IC_{50}$ DYRK1A (μM) | $R^1$ | $NHR^3$ | $Ar^1$ | Reaction used |
|---|---|---|---|---|---|
| ST092 | >10 | Me | NHn-Pr | 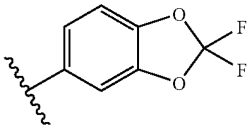 | D Oil bath |
| FCFD14 | >10 | Me | NHn-Pr | 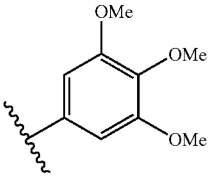 [SMILES: *c1cc(OC)c(OC)c(OC)c1] | D Oil bath |
| FC104b | >10 | Me | NHi-Pr | 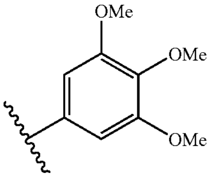 [SMILES: *c1cc(OC)c(OC)c(OC)c1] | D Oil bath |
| FCFD11 | >10 | Me | NHn-Pr | 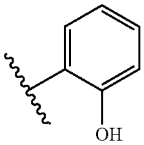 [SMILES: *c1ccccc1O] | D Oil bath |
| FCFD08 | >10 | Me | NHn-Pr | 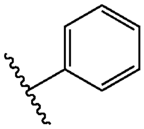 [SMILES: *c1ccccc1] | D Oil bath |
| FC095 | >10 | Me | NHi-Pr | 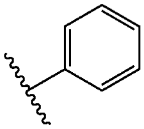 [SMILES: *c1ccccc1] | D Oil bath |
| FC092 | >10 | Me | NHn-Pr | 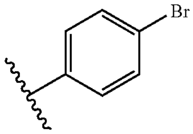 | D Oil bath |
| FC109 | >10 | Me | NHi-Pr | 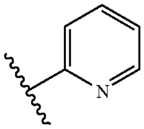 [SMILES: *c1ccccn1] | D Oil bath |
| SA164 | >10 | n-Bu | 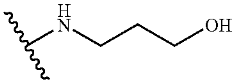 [SMILES: *NCCCO] | 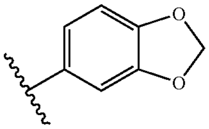 [SMILES: *c1ccc2c(c1)OCO2] | D Microwave |

-continued
| | | | | | |
|---|---|---|---|---|---|
| JR442 | >10 | n-Bu | NHn-Pr | 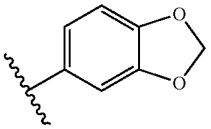 [SMILES: *c1ccc2c(c1)OCO2] | D<br>Oil bath |
| FCJR464 | >10 | n-Bu | NHn-Bu | 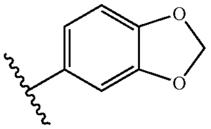 [SMILES: *c1ccc2c(c1)OCO2] | D<br>Oil bath |
| JR445 | >10 | Ph | NHn-Pr | 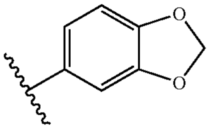 [SMILES: *c1ccc2c(c1)OCO2] | D<br>Oil bath |
| FC085 | 1.7 | H | NHMe | 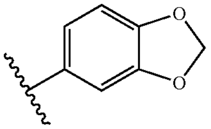 [SMILES: *c1ccc2c(c1)OCO2] | F |
| FC090 | 1.1 | H | NHEt | 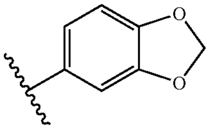 [SMILES: *c1ccc2c(c1)OCO2] | F |
| FC126 | 0.89 | H | NHn-Pr | 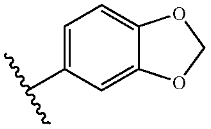 [SMILES: *c1ccc2c(c1)OCO2] | F |
| MADE44 | 0.071 | H | 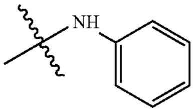 [SMILES: *Nc1ccccc1] | 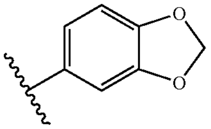 [SMILES: *c1ccc2c(c1)OCO2] | D<br>Microwave |
| MADE48 | 0.084 | H | 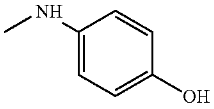 | 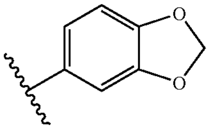 [SMILES: *c1ccc2c(c1)OCO2] | D<br>Microwave |
| FC114 | 0.5 | H | 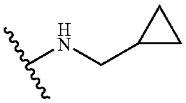 [SMILES: *NCC1CC1] | 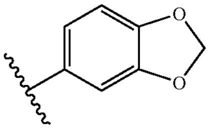 [SMILES: *c1ccc2c(c1)OCO2] | F |
| ST325 | 0.17 | H | $NH_2$ | 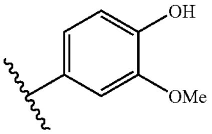 [SMILES: *c1ccc(O)c(OC)c1] | F |
| ST326 | >10 | H | $NH_2$ | 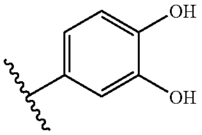 [SMILES: *c1ccc(O)c(O)c1] | F |

-continued

| | | | | | |
|---|---|---|---|---|---|
| ST033 | 0.3 | Me | 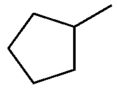 | 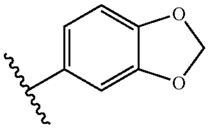 [SMILES: *c1ccc2c(c1)OCO2] | F |

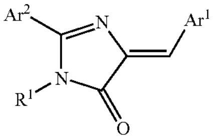

7

| Molecule reference | $IC_{50}$ DYRK1A (μM) | $R^1$ | $Ar^2$ | $Ar^1$ | Reaction used |
|---|---|---|---|---|---|
| NL39 | 3.2 | Me | Ph | 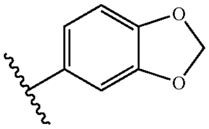 [SMILES: *c1ccc2c(c1)OCO2] | H |
| NL96 | 0.43 | Me | $C_6H_5$-pOH | 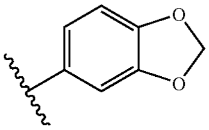 [SMILES: *c1ccc2c(c1)OCO2] | H |
| NL88A | 0.22 | Me | 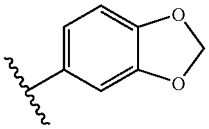 [SMILES: *c1ccc2c(c1)OCO2] | 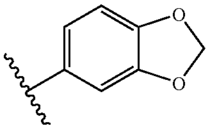 [SMILES: *c1ccc2c(c1)OCO2] | H |

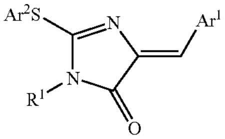

8

| Molecule reference | IC50 DYRK1A (mM) | $R^1$ | $SAr^2$ | $Ar^1$ | Reaction used |
|---|---|---|---|---|---|
| ST379 | 1.9 | Me | 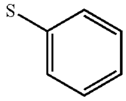 | 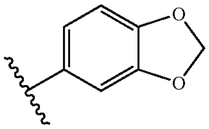 [SMILES: *c1ccc2c(c1)OCO2] | I |
| ST385 | >10 | Me | 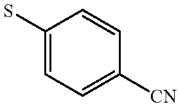 | 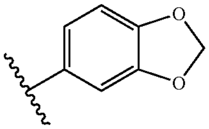 [SMILES: *c1ccc2c(c1)OCO2] | I |

References:
1: Microwave mediated solventless synthesis of new derivatives of marine alkaloid Leucettamine B.
Jean René Chérouvrier, François Carreaux, Jean Pierre Bazureau
Tetrahedron Letters 2002, 43, 3581-3584.
2: Parallel solution phase synthesis of 2-alkylthio-3,5-dihydro-4H-imidazol-4-one by one-pot three component domino reaction.
Stéven Renault, Sarah Bertrand, François Carreaux*, Jean Pierre Bazureau*.
Journal of Combinatorial Chemistry 2007, 9, accepted for publication (awaiting authorization for ACS in ASAP).
3: Synthesis of the marine alkaloid Leucettamine B
Nathalie Roué, Ian Bergman
Tetrahedron 1999, 55, 14729-14738.
4: The isolation and synthesis of polyandrocarpamines A and B. Two new 2-aminoimidazolone compounds from the Fidjian ascidian, *Polyandrocarpa* sp.
Rohan A. Davis, William Aalbersberg, Semisi Meo, Rosan Moreira da Rocha, Chris M. Ireland
Tetrahedron 2002, 58, 3263-3269.

The invention claimed is:

1. An imidazolone derivative, characterized in that said derivative corresponds to formula (I)

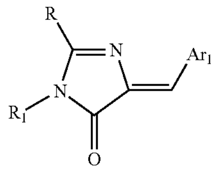

I in which:

$R_1$ represents a $C_1$-$C_3$ alkyl radical or a hydrogen atom, and/or an aryl radical $Ar_1$ is chosen from

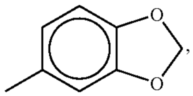,

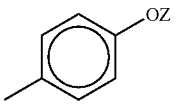

or

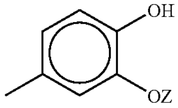

R represents an $R_2$—S— group, $R_2$ then being chosen from radicals represented by $T_1$-$(CH_2)_n$, with n=0, 1, 2 or 3 and $T_1$ representing one of the following radicals: methyl, vinyl, alkyl, alkynyl, nitrile, cycloalkyl, which may be $C_3$ or $C_4$, Z—O, Z—CO, with Z═$C_1$-$C_3$ alkyl, or hal, hal representing F, Cl, Br or I or a $CCl_3$ group, or an $R_3$—NH— group, $R_3$ then being chosen from radicals represented by $T_2$-$(CH_2)_n$, with n=0, 1 or 2, and $T_2$ representing one of the following radicals: methyl, vinyl, ZO, ZO—CONH—, —CH—$(OZ)_2$, ZCO, with Z═H or linear or branched $C_1$-$C_4$ alkyl, $NH_2$, $C_3$ cycloalkyl, aryl or substituted aryl, or $R_2$═H, or an $R_4$—CONH— group, $R_4$ then being a branched $C_3$-$C_5$ alkyl radical, or $Ar_2$ or $Ar_2$—S, $Ar_2$ being chosen from a phenyl, substituted phenyl or benzodioxolyl radical, and an $IC_{50}$ of less than 5 μM.

2. The derivative as claimed in claim 1, characterized in that it has an $IC_{50}$ of less than 1 μM and corresponds to formula (I) in which:

$R_1$ represents H or $CH_3$ $Ar_1$ represents the radical

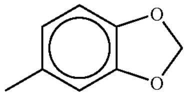

or

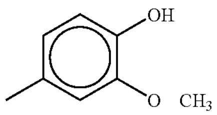

$R_3$ represents an $R_2$—S— group, $R_2$ then being chosen from radicals represented by $T_1$-$(CH_2)_n$, with $T_1$=a methyl, alkynyl, nitrile, hal, $CH_3O$, cyclopropyl or cyclobutyl radical, n=0, 1, 2 or 3, "hal" representing a halogen atom or a $CCl_3$ group, or an $R_3$—HN— group, $R_3$ then being chosen from radicals represented by $T_2$-$(CH_2)_n$, with $T_2$=$C_3$ alkyl, OH, cyclopropyl, phenyl, phenyl substituted with OH, $OCH_3$, COOH and OH, $CH_2OH$, $C(CH_3, OH)$, $CH_2$—$CH_2OH$, $CH_2$—COOH or benzodioxolyl, or $R_2$═H, n=0, 1 or 2, or an $Ar_2$ group chosen from a para-hydroxyphenyl or benzodioxolyl group.

3. The derivative as claimed in claim 1, characterized in that it is chosen from the derivatives of formula (I) in which

R═$R_2$S $R_2$═$CH_2C$≡CH; $R_1$=Me; $Ar_1$=1,3-benzodioxol-5-yl
$R_2$═$CH_2C$≡N; $R_1$=Me; $Ar_1$=1,3-benzodioxol-5-yl
$R_2$═$CH_2CH_2Cl$; $R_1$=Me; $Ar_1$=1,3-benzodioxol-5-yl
$R_2$═$CH_3$; $R_1$═H; $Ar_1$=1,3-benzodioxol-5-yl
$R_2$═$CH_2CH_3$; $R_1$═H; $Ar_1$=1,3-benzodioxol-5-yl
$R_2$═$CH_2CH_2CH_3$; $R_1$═H; $Ar_1$=1,3-benzodioxol-5-yl
$R_2$═$CH(CH_3)_2$; $R_1$═H; $Ar_1$=1,3-benzodioxol-5-yl
$R_2$═$CH_2C$≡N; $R_1$═H; $Ar_1$=1,3-benzodioxol-5-yl
$R_2$═$CH_2(CH_2)_2CH_3$; $R_1$═H; $Ar_1$=1,3-benzodioxol-5-yl
$R_2$═$CH_2CH_2OCH_3$; $R_1$═H; $Ar_1$=1,3-benzodioxol-5-yl
$R_2$═$CH_2T_1$ with $T_1$=cyclopropyl; $R_1$═H; $Ar_1$=1,3-benzodioxol-5-yl
$R_2$═$CH_2T_1$ with $T_1$=cyclobutyl; $R_1$═H; $Ar_1$=1,3-benzodioxol-5-yl

R═$R_3$NH $R_3$═$CH_2CH_3$; $R_1$=Me; $Ar_1$=1,3-benzodioxol-5-yl
$R_3$═$CH_2CH_2OH$; $R_1$=Me; $Ar_1$=1,3-benzodioxol-5-yl
$R_3$═$CH_2T_1$ with $T_1$=cyclopropyl; $R_1$=Me; $Ar_1$=1,3-benzodioxol-5-yl
$R_3$═$CH_2CH_3$; $R_1$=Me; $Ar_1$=1,3-benzodioxol-5-yl
$R_3$=o-HO—$C_6H_4$; $R_1$=Me; $Ar_1$=1,3-benzodioxol-5-yl
$R_3$═$C_6H_5$; $R_1$=Me; $Ar_1$=1,3-benzodioxol-5-yl
$R_3$=p-HO—$C_6H_4$; $R_1$=Me; $Ar_1$=1,3-benzodioxol-5-yl
$R_3$=p-HO-m-$HO_2C$—$C_6H_3$; $R_1$=Me; $Ar_1$=1,3-benzodioxol-5-yl
$R_3$=p-m-$OCH_2O$—$C_6H_3$; $R_1$=Me; $Ar_1$=1,3-benzodioxol-5-yl
$R_3$=p-$CH_3$—$C_6H_4$; $R_1$=Me; $Ar_1$=1,3-benzodioxol-5-yl
$R_3$═$HOCH_2CHOHCH_2$; $R_1$=Me; $Ar_1$=1,3-benzodioxol-5-yl
$R_3$=p-m-$OCH_2CH_2O$—$C_6H_3$; $R_1$=Me; $Ar_1$=1,3-benzodioxol-5-yl
$R_3$=p-$CH_3O$—$C_6H_4$; $R_1$=Me; $Ar_1$=1,3-benzodioxol-5-yl
$R_3$=m-$HOCH_2$—$C_6H_4$, $R_1$=Me; $Ar_1$=1,3-benzodioxol-5-yl
$R_3$=m-$HOCH(CH_3)$—$C_6H_4$; $R_1$=Me; $Ar_1$=1,3-benzodioxol-5-yl
$R_3$=p-$HOCH_2CH_2$—$C_6H_4$; $R_1$=Me; $Ar_1$=1,3-benzodioxol-5-yl
$R_3$=p-$HO_2CCH_2O$—$C_6H_4$; $R_1$=Me; $Ar_1$=1,3-benzodioxol-5-yl
$R_3$═$CH_2CH_2CH_3$; $R_1$═H; $Ar_1$=1,3-benzodioxol-5-yl
$R_3$═$CH_2T_1$ with $T_1$=cyclopropyl; $R_1$═H; $Ar_1$=1,3-benzodioxol-5-yl
$R_3$═$C_6H_5$; $R_1$═H; $Ar_1$=1,3-benzodioxol-5-yl
$R_3$=p-HO—$C_6H_4$; $R_1$═H; $Ar_1$=1,3-benzodioxol-5-yl
$R_3$═H; $R_1$═H; $Ar_1$=p-HO-m-MeO—$C_6H_3$ R═$Ar_2$ $Ar_2$=p-HO—$C_6H_4$; $R_1$=Me; $Ar_1$=1,3-benzodioxol-5-yl $Ar_2$=p-m-$OCH_2O$—$C_6H_3$; $R_1$=Me; $Ar_1$=1,3-benzodioxol-5-yl.

4. A pharmaceutical composition, characterized in that it contains a therapeutically effective amount of at least one derivative as claimed in claim 1.

* * * * *